US010665346B2

(12) United States Patent
Baker

(10) Patent No.: US 10,665,346 B2
(45) Date of Patent: *May 26, 2020

(54) NETWORK FOR MEDICAL IMAGE ANALYSIS, DECISION SUPPORT SYSTEM, AND RELATED GRAPHICAL USER INTERFACE (GUI) APPLICATIONS

(71) Applicant: Progenics Pharmaceuticals, Inc., New York, NY (US)

(72) Inventor: Mark R. Baker, New York, NY (US)

(73) Assignee: Progenics Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/718,839

(22) Filed: Dec. 18, 2019

(65) Prior Publication Data

US 2020/0126666 A1    Apr. 23, 2020

Related U.S. Application Data

(63) Continuation of application No. 16/418,527, filed on May 21, 2019, which is a continuation of application
(Continued)

(51) Int. Cl.
*G06Q 10/00* (2012.01)
*G06K 9/00* (2006.01)
(Continued)

(52) U.S. Cl.
CPC ....... *G16H 50/20* (2018.01); *G01N 33/57434* (2013.01); *G16H 15/00* (2018.01);
(Continued)

(58) Field of Classification Search
USPC ........ 382/100, 103, 128–134, 154–158, 162, 382/168, 173, 181, 206, 209, 220, 224,
(Continued)

(56) References Cited

U.S. PATENT DOCUMENTS 7,450,747 B2   11/2008   Jabri et al.
7,970,194 B2   6/2011    Kimura
(Continued)

FOREIGN PATENT DOCUMENTS

EP   1426903 A2   6/2004
EP   1508872 A1   2/2005
(Continued)

OTHER PUBLICATIONS

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).
(Continued)

*Primary Examiner* — Seyed H Azarian
(74) *Attorney, Agent, or Firm* — Ronen Adato; William R. Haulbrook; Choate, Hall and Stewart LLP

(57) ABSTRACT

Described herein is a platform and supported graphical user interface (GUI) decision-making tools for use by medical practitioners and/or their patients, e.g., to aide in the process of making decisions about a course of cancer treatment and/or to track treatment and/or the progress of a disease.

13 Claims, 11 Drawing Sheets

Related U.S. Application Data

No. 15/794,220, filed on Oct. 26, 2017, now Pat. No. 10,340,046.

(60) Provisional application No. 62/413,936, filed on Oct. 27, 2016.

(51) Int. Cl.
| | |
|---|---|
| G16H 50/20 | (2018.01) |
| G16H 30/20 | (2018.01) |
| G16H 30/40 | (2018.01) |
| G16H 50/70 | (2018.01) |
| G16H 50/30 | (2018.01) |
| G16H 15/00 | (2018.01) |
| G01N 33/574 | (2006.01) |

(52) U.S. Cl.
CPC .............. *G16H 30/20* (2018.01); *G16H 30/40* (2018.01); *G16H 50/30* (2018.01); *G16H 50/70* (2018.01)

(58) Field of Classification Search
USPC ..... 382/232, 254, 286–295, 305, 312; 705/2
See application file for complete search history.

(56) References Cited

U.S. PATENT DOCUMENTS

| | | | |
|---|---|---|---|
| 8,211,401 | B2 | 7/2012 | Babich et al. |
| 8,538,166 | B2 | 9/2013 | Gordon et al. |
| 8,705,887 | B2 | 4/2014 | Ma et al. |
| 8,778,305 | B2 | 7/2014 | Pomper et al. |
| 8,855,387 | B2 | 10/2014 | Hamadeh et al. |
| 8,962,799 | B2 | 2/2015 | Babich et al. |
| 9,002,081 | B2 * | 4/2015 | Brown .................. G06T 7/0014 382/128 |
| RE47,609 | E | 9/2019 | Hamadeh et al. |
| 2003/0215120 | A1 | 11/2003 | Uppaluri et al. |
| 2006/0062425 | A1 * | 3/2006 | Shen ........................ G06T 15/08 382/100 |
| 2007/0081712 | A1 * | 4/2007 | Huang ....................... G06T 7/38 382/128 |
| 2007/0081713 | A1 | 4/2007 | Jerebko |
| 2007/0100225 | A1 | 5/2007 | Maschke |
| 2015/0110716 | A1 | 4/2015 | Armor |
| 2015/0331995 | A1 * | 11/2015 | Zhao ........................ G16Z 99/00 705/2 |
| 2016/0203263 | A1 * | 7/2016 | Maier .................... G16H 50/30 705/2 |
| 2016/0335395 | A1 * | 11/2016 | Wu ........................ G06F 19/321 |
| 2017/0083682 | A1 * | 3/2017 | McNutt .................. G16H 50/30 |
| 2018/0144828 | A1 | 5/2018 | Baker |

FOREIGN PATENT DOCUMENTS

| | | |
|---|---|---|
| WO | WO-9905503 A2 | 2/1999 |
| WO | WO-2007/062135 A2 | 5/2007 |
| WO | WO-2009/084995 A1 | 7/2009 |
| WO | WO-2018/081354 A1 | 5/2018 |

OTHER PUBLICATIONS

Anand, A. et al., Automated Bone Scan Index as a quantitative imaging biomarker in metastatic castration-resistant prostate cancer patients being treated with enzalutamide, EJNMMI Research, 6:23, 7 pages (2016).
Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, presented Feb. 16, 2017.
Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).
Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).
Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138 (2017).
Armstrong, A. J. et al., Phase 3 prognostic analysis of the automated bone scan index (aBSI) in men with bone-metastatic castration-resistant prostate cancer (CRPC), Meeting Library ASC University, 1 page abstract, (2017).
Belal, S. et al., Association of PET Index quantifying skeletal uptake in NaF PET/CT images with overall survival in prostate cancer patients, ASCO GU 2017, Poster 178, presented Feb. 16, 2017.
Belal, S. et al., PET Index quantifying skeletal uptake in NaF PET/CT images with overall survival in prostate cancer patients, ASCO GU 2017, Abstract (Feb. 13, 2017).
Belal, S. L. et al, 3D skeletal uptake of $^{18}$F sodium fluoride in PET/CT images is associate with overall survival in patients with prostate cancer, EJNMMI Research, 7(15):1-8 (2017).
Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).
Bushberg, J. T. et al., Essential Physics of Medical Imaging, Essential Physics of Medical Imaging, 19.3: p. 581 (table 15-3), p. 713 paragraph 6, section 19.3 and p. 720, (2011).
Dennis, E. et al., Bone Scan Index: A Quantitative Treatment Response Biomarker for Castration-Resistant Metastatic Prostate Cancer, Journal of Clinical Oncology, 30(5):519-524 (2012).
Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).
GE Healthcare, SPECT/CT Cameras, retrieved Oct. 25, 2017: <http://www3.gehealthcare.com.sg/en-gb/products/categories/nuclear_medicine/spect-ct_cameras>.
Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).
Goffin, K. E. et al., Phase 2 Study of 99mTc-trofolastat SPECT/CT to identify and localize prostate cancer in intermediate- and high-risk patients undergoing radical prostatectomy and extended pelvic lymph node dissection, Journal of Nuclear Medicine, pp. 1-22 with supplemental data included, (2017).
Guimond, A. et al., Average Brain Models: A Convergence Study, Computer Vision and Image Understanding, 77:192-210 (2000).
Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).
Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.
Horikoshi, H. et al., Computer-aided diagnosis system for bone scintigrams from Japanese patients: importance of training database, Annals of Nuclear Medicine, 26(8):622-626 (2012).
Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).
International Search Report, International Application No. PCT/US2017/058418 (Network for Medical Image Analysis, Decision Support System, and Related Graphical User Interface (GUI) Applications, filed Oct. 26, 2017), issued by ISA/European Patent Office, 4 pages, dated Feb. 27, 2018.

(56) References Cited

OTHER PUBLICATIONS

Kaboteh R. et al., Progression of bone metastases in patients with prostate cancer—automated detection of new lesions and calculation of bone scan index, EJNMMI Research, 3:64 (2013).
Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).
Keiss, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultrasuond CT MR 31(6):496-505 (2010) retrieved Oct. 25, 2017: <https://www.ncbi.nlm.nih.gov/pmc/articles/PMC3026294/>.
Knutsson, H., and Andersson, M., Morphons: Segmentation using Elastic Canvas and Paint on Priors, IEEE International Conference on Image Processing (ICIP 2005), Genova, Italy, 4 pages. (2005).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Litjens, G. et al., A survey on deep learning in medical image analysis, Medical Image Analysis, 42:60-88, (2017).
Liu, L. et al., Computer-Aided Detection of Prostate Cancer with MRI: Technology and Applications, Acad Radiol. Author manuscript, 50 pages 2016.
Ma, L. et al., Automatic segmentation of the prostate on CT images using deep learning and multi-atlas fusion, Proc. of SPIE vol. 10133:101332O-1-101332O-9 (2017).
Ma, L. et al., Combining Population and Patient-Specific Characteristics for Prostate Segmentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.
Nakajima, K. et al., Enhanced diagnostic accuracy for quantitative bone scan using an artificial neural network system: a Japanese multi-center database project, EJNMMI Research, 3:83 (2013).
National Cancer Institute, NCI Drug Dictionary: gallium Ga 68-labeled PSMA-11, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, retrieved Oct. 25, 2017: <https://www.cancer.gov/publications/dictionaries/cancer-drug?cdrid=537722>.
Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).
Polymeri, E. et al., Analytical validation of an automated method for segmentation of the prostate gland in CT images, EJNMMI, EANM '17, 44(Suppl 2):S119-S956, Abstract EP-0641 (2017).
radiologyinfo.org for Patients, Computed Tomography (CT), retrieved Oct. 25, 2017: <https://www.radiologyinfo.org/en/submenu.cfm?pg=ctscan>.
Rowe, S. P. et al., PET Imaging of prostate-specific membrane antigen in prostate cancer: current state of the art and future challenges, Prostate Cancer and Prostatic Diseases, 1-8 (2016).
Rowe, S. P. et al., PSMA-Based [$^{18}$F]DCFPyL PET/CT Is Superior to Conventional Imaging for Lesion Detection in Patients with Metastatic Prostate Cancer, Mol Imaging Biol, 18:411-419, (2016).
Sabbatini, P. et al., Prognostic Significance of Extent of Disease in Bone in Patients With Androgen-Independent Prostate Cancer, Journal of Clinical Oncology, 17(3):948-957 (1999).
Sadik, M. et al., 3D prostate gland uptake of 18F-choline—association with overall survival in patients with hormone-naïve prostate cancer, The Journal of Nuclear Medicine, 58(Suppl. 1):Abstract 544 (2017).
Sadik, M. et al., A new computer-based decision-support system for the interpretation of bone scans, Nuclear Medicine Communications, 27(5):417-423 (2006).
Sadik, M. et al., Automated 3D segmentation of the prostate gland in CT images—a first step towards objective measurements of prostate uptake in PET and SPECT images, Journal of Nuclear Medicine, 58(1):1074, (2017).
Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).
Sadik, M. et al., Computer-assisted interpretation of planar whole-body bone scans, Journal Nuclear Medicine, 49(12):1958-65, 2008.
Sadik, M. et al., Convolutional neural networks for segmentation of 49 selected bones in CT images show high reproducibility, EJNMMI, EANM '17, 44(Suppl 2):S119-S956, Abstract OP-657 (2017).
Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.
Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).
Sajn, L. et al., Computerized segmentation of whole-body bone scintigrams and its use in automated diagnostics, Computer Methods and Programs in Biomedicine, 80:47-55 (2005).
Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).
Sjöstrand K. et al., Statistical regularization of deformation fields for atlas-based segmentation of bone scintigraphy images, MICCAI 5761:664-671 (2009).
Sluimer, I. et al., Toward Automated Segmentation of the Pathological Lung in CT, IEEE Transactions on Medical Imaging, 24(8):1025-1038 (2005).
Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of SPIE 10135:101351L-1-101351L-6 (2017).
Tian, Z., et al., Superpixel-based Segmentation for 3D Prostate MR Images, IEEE Trans Med Imaging, Author manuscript, 32 pages, (2016).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
Wrangsjo, A. et al., Non-rigid Registration Using Morphons, Proceedings of the 14th Scandinavian Conference on Image Analysis (SCIA '05), pp. 501-510 (2005).
Written Opinion, International Application No. PCT/US2017/058418 (Network for Medical Image Analysis, Decision Support System, and Related Graphical User Interface (GUI) Applications, filed Oct. 26, 2017), issued by ISA/European Patent Office, 9 pages, dated Feb. 27, 2018.
Yin, T.-K., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

\* cited by examiner

FIG. 3

(I) RECEIVING AND STORING SETS OF MEDICAL IMAGES IN A DATABASE (II) ACCESSING ONE OR MORE OF THE MEDICAL IMAGES FOR TRANSMISSION TO THE USER FOR DISPLAY ON A USER COMPUTING DEVICE (III) AUTOMATICALLY ANALYZING, BY THE PROCESSOR, THE MEDICAL IMAGES TO COMPUTE A RISK INDEX (E.G., BSI) AND/OR TO GENERATE A RISK MAP (IV) GENERATING A RADIOLOGIST REPORT FOR A PATIENT ACCORDING TO THE PATIENT IMAGES AND/OR RISK INDEX/ RISK MAP (V) APPLYING A MACHINE LEARNING ALGORITHM TO UPDATE A PROCESS FOR THE AUTOMATIC ANALYSIS OF FUNCTION (III)

FIG. 6

NETWORK FOR MEDICAL IMAGE ANALYSIS, DECISION SUPPORT SYSTEM, AND RELATED GRAPHICAL USER INTERFACE (GUI) APPLICATIONS

CROSS REFERENCE TO RELATED APPLICATIONS

This application is a continuation of U.S. application Ser. No. 16/418,527, filed May 21, 2019, which is a continuation of U.S. application Ser. No. 15/794,220, filed Oct. 26, 2017 (now U.S. Pat. No. 10,340,046, issued Jul. 2, 2019), which claims the benefit of U.S. Provisional Application 62/413,936, filed on Oct. 27, 2016, the content of each of which are hereby incorporated by reference herein in their entirety.

TECHNICAL FIELD

This invention relates generally to systems and methods for creation, analysis, and/or presentation of medical image data. More particularly, in certain embodiments, the invention relates to a cloud-based platform and supported GUI decision-making tools for use by medical practitioners and/or their patients, e.g., to aide in the process of making decisions about a course of cancer treatment and/or to track treatment and/or the progress of a disease.

BACKGROUND

Targeted image analysis involves the use of radiolabeled small molecules that bind to specific receptors, enzymes and proteins in the body that are altered during the evolution of disease. After administration to a patient, these molecules circulate in the blood until they find their intended target. The bound radiopharmaceutical remains at the site of disease, while the rest of the agent clears from the body. The radioactive portion of the molecule serves as a beacon so that an image may be obtained depicting the disease location and concentration using commonly available nuclear medicine cameras, known as single-photon emission computerized tomography (SPECT) or positron emission tomography (PET) cameras, found in most hospitals throughout the world. Physicians can then use this information to determine the presence and the extent of disease in a patient. The physician can use this information to provide a recommended course of treatment to the patient and to track the progression of disease.

There are a variety of software-based analytical techniques available for analysis and enhancement of PET and SPECT images that can be used by a radiologist or physician. There are also a number of radiopharmaceuticals available for imaging particular kinds of cancer. For example, the small molecule diagnostic 1404 targets the extracellular domain of prostate specific membrane antigen (PSMA), a protein amplified on the surface of >95% of prostate cancer cells and a validated target for the detection of primary and metastatic prostate cancer. 1404 is labeled with technetium-99m, a gamma-emitter isotope that is widely available, relatively inexpensive, facilitates efficient preparation, and has spectrum characteristics attractive for nuclear medicine imaging applications.

Another example radiopharmaceutical is PyL™ (also known as [$^{18}$F]DCFPyL), which is a clinical-stage, fluorinated PSMA-targeted PET imaging agent for prostate cancer. A proof-of-concept study published in the April 2015 issue of the Journal of Molecular Imaging and Biology demonstrated that PET imaging with PyL™ showed high levels of PyL™ uptake in sites of putative metastatic disease and primary tumors, suggesting the potential for high sensitivity and specificity in detecting prostate cancer.

An oncologist may use images from a targeted PET or SPECT study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the PET or SPECT images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results.

If an imaging study shows that the patient has a particular disease or condition (e.g., cancer), the physician discusses various treatment options, including surgery, as well as risks of doing nothing or adopting a watchful waiting or active surveillance approach, rather than having surgery.

There are limitations associated with this process, both from the perspective of the physician and from the perspective of the patient. While the radiologist's report is certainly helpful, the physician must ultimately rely on her experience in formulating an assessment and recommendation for her patient. Furthermore, the patient must place a great deal of trust in his physician. The physician may show the patient his PET/SPECT images and may tell the patient a numerical risk associated with various treatment options or likelihood of a particular prognosis, but the patient may very well struggle to make sense of this information. Moreover, the patient's family will likely have questions, particularly if cancer is diagnosed but the patient opts not to have surgery. The patient and/or his family members may search online for supplemental information and may become misinformed about risks of the diagnosed condition. A difficult ordeal may become more traumatic.

Thus, there remains a need for systems and methods for improved analysis of medical imaging studies and communication of those results, diagnoses, prognoses, treatment recommendations, and associated risks to a patient.

SUMMARY OF THE INVENTION

Presented herein is a cloud-based platform and supported graphical user interface (GUI) decision-making tools for use by medical practitioners and/or their patients, e.g., to aide in the process of making decisions about a course of cancer treatment and/or to track treatment and/or the progress of a disease.

For example, presented herein is a network-based (e.g., cloud-based) support platform allowing multiple users to store, access, analyze, and/or provide feedback regarding a given set of image data for a patient; platform supports software tools for automated analysis of targeted PET/ SPECT/or other image(s), generation of radiologist reports, and application of machine learning algorithms to update process by which images are analyzed (e.g. updating segmentation and/or classification routines based on growing image database). In certain embodiments, the targeted PET/ SPECT image(s) may be obtained using PyL™ and/or 1404 as the radiopharmaceutical(s). In certain embodiments, multiple (accredited) users can access the information, e.g., to weigh in on data interpretation.

Also presented herein is a software tool (e.g., mobile app) featuring a graphical user interface (GUI) element with controls for adjusting presentation of a 3D risk image corresponding to a patient organ (and/or other tissue) for comparison with reference images (e.g., for use in communication of results to patient as a decision-making support). For example, the tool may be supported by the network-based support platform above. This tool can provides an easily-understood, user-friendly, interactive, controllable pictorial display to communicate information about a patient's condition to the patient (and/or to the physician, or to the patient's family with the patient's permission). For example, a patient for whom a risk of cancer is detected can display a map indicating areas and/or degrees of risk and can compare this risk map with those of others for whom a given course of treatment is recommended. For instance, this tool can help a patient in his decision whether or not to have surgery (e.g., for a detected risk of prostate cancer). The patient can visually compare his risk map with a map representing a typical risk-level for which surgery would be recommended, below which it may be reasonable to opt not to have surgery and engage in watchful waiting or active surveillance. Thus, a low-risk patient who is told by his physician that he has a non-zero risk of cancer may find comfort in a visual, controllable comparison between his situation and that of someone (e.g., where the reference to which the patient's risk situation is compared can be tuned for age, weight, and/or other risk factors of the patient).

In one aspect, the invention is directed to a network-based (e.g., cloud based) decision support system comprising: a processor (e.g., of a network or Internet host server); and a memory having instructions stored thereon, wherein the instructions, when executed by the processor, cause the processor to perform one or more of functions (i) to (v) as follows: (i) receive and store medical images [e.g., comprising one or more of the following: targeted PET images, targeted SPECT images, computed tomography (CT) images, magnetic resonance (MR) images, ultrasound (US) images, gamma camera (i.e. scintillation camera) images, and combinations, fusions, or derivatives of any of the above] in a database [e.g., wherein the targeted PET/SPECT/ gamma camera image(s) are obtained using one or more radiopharmaceuticals (e.g., [18F]DCFPyL and/or 1404 and/ or a composition comprising technetium 99m, {e.g., technetium 99m methylenediphosphonate ($^{99m}$Tc MDP)}), and/ or wherein the medical images are obtained using non-radioactive agents or no agents], each medical image associated with a particular patient; (ii) access one or more of the medical images and/or related data associated with a particular patient from the database upon user request (e.g., following automated verification that the user is properly credentialed for receiving the requested images and/or data) for transmission to the user for display on a user computing device; (iii) automatically analyze one or more of the medical images [e.g., to generate a risk index (e.g., BSI) and/or a risk map, e.g., a visual representation (e.g., 3D representation) of tissue (e.g., an organ or other part of the body) with graphical denotations (e.g., texture- or color-coding) marking regions of risk of current disease or risk of recurrence of disease, e.g., cancer, e.g., wherein the risk map is displayed as an overlay of the PET/SPECT/CT/MRI/US/ combined/derived/fused image of the tissue, or is in place of the image of the tissue]; (iv) generate a radiologist report for a patient according to one or more of the medical images for the patient; and (v) apply a machine learning algorithm to update a process for automatically analyzing one or more of the medical images using accumulated image data in the database [e.g., wherein the automatic analysis of the one or more medical images in (iii) and/or (v) above comprises any one or more of (a) to (d) as follows: (a) automated fusion of the (e.g., PET, SPECT, CT, Mill, and/or US) image(s) of the tissue; (b) geographic identification of one or more organs, organ structures, sub-organs, organ regions, and/or other regions of the imaged tissue of the patient and production of a 3D image of the geographically identified tissue with PET, SPECT, CT, MM, and/or US data overlaid; (c) computation of risk information comprising one or more risk indices, a risk field, or a risk map using data from the database, the image(s) of the tissue, and/or the 3D image in (b); and (d) use of the risk information computed in (c) (e.g., and data from the database) to produce a 3D risk picture for the patient].

In certain embodiments, the medical images in the database comprise a series of medical images of a first patient taken over time (e.g., over the course of multiple visits to one or more doctors), and wherein the instructions cause the processor to determine a value of at least a first risk index for each medical image of the series, thereby tracking determined values of at least the first risk index for the first patient over time.

In certain embodiments, the medical images comprise a single-photon emission computerized tomography (SPECT) scan of a first patient obtained (e.g., to identify one or more hotspots) following administration to the first patient of an imaging agent comprising 1404 labeled with $^{99m}$Tc, and a computed tomography (CT) scan (e.g., to identify anatomical features) of the first patient, wherein the instructions cause the processor to overlay the SPECT scan with the CT scan to create a composite image (SPECT-CT) of the first patient.

In certain embodiments, the medical images comprise a positron emission tomography (PET) scan of a first patient obtained (e.g., to identify one or more hotspots) following administration to the first patient of an imaging agent comprising [18F]DCFPyL (DCFPyL labeled with $^{18}$F), and a CT scan of the first patient, wherein the instructions cause the processor to overlay the PET scan with the CT scan to create a composite image (PET-CT) of the first patient.

In certain embodiments, the medical images comprise a whole-body scan (e.g., including anterior and posterior views) of a first patient made with a gamma camera following administration to the first patient of an imaging agent comprising technetium 99m methylenediphosphonate ($^{99m}$Tc MDP).

In certain embodiments, the medical images comprise a composite image of a first patient, the composite image comprising a CT scan overlaid with a nuclear medicine image (e.g., a SPECT scan; e.g., a PET scan) obtained at substantially the same time as the CT scan and following administration to the first patient of an imaging agent comprising a Prostate Specific Membrane Antigen (PSMA) binding agent comprising (e.g., labelled with) a radionuclide, and the instructions cause the processor to automatically analyze the composite image by: (a) using the composite image to geographically identify a 3D boundary for each of one or more regions of imaged tissue [e.g., organs (e.g., a prostate; e.g., a liver; e.g., lungs or a lung; e.g., lymph nodes), organ structures, sub-organs, organ regions, and/or other regions (e.g., one or more particular bones; e.g., a skeletal region of the patient), e.g., regions of interest] within the nuclear medicine image (e.g., such that portions of the nuclear medicine image falling within and/or outside of the 3D boundaries can be differentiated from each other); and (c) computing (i) a value of each of one or more risk indices and/or (ii) a risk map using the nuclear medicine image with the identified 3D boundaries of the one or more region(s).

In certain embodiments, the instructions cause the processor to, for at least one risk index of the one or more risk indices, compute the value of the risk index by: determining, for each of the one or more regions, a corresponding cancerous tissue level within the region based on intensity values of the nuclear medicine image within the 3D boundary of the region (e.g., by identifying within the nuclear medicine image, a plurality of hotspots within the 3D boundary of the region and computing a total number of and/or a total volume of the identified hotspots); and computing the value of the risk index based on the determined cancerous tissue levels within the one or more regions.

In certain embodiments, the nuclear medicine image is a SPECT scan.

In certain embodiments, the imaging agent comprises a metal chelated to the PSMA binding agent, and wherein the metal is the radionuclide [e.g., wherein the metal is a radioisotope of technetium (Tc) (e.g., wherein the metal is technetium-99m ($^{99m}$Tc)); e.g., wherein the metal is a radioisotope of rhenium (Re) (e.g., wherein the metal is rhenium-188 ($^{188}$Re); e.g., wherein the metal is rhenium-186 ($^{86}$Re)); e.g., wherein the metal is a radioisotope of yttrium (Y) (e.g., wherein the metal is $^{90}$Y); e.g., wherein the metal is a radioisotope of lutetium (Lu)(e.g., wherein the metal is $^{177}$Lu); e.g., wherein the metal is a radioisotope of gallium (Ga) (e.g., wherein the metal is $^{68}$Ga; e.g., wherein the metal is $^{67}$Ga); e.g., wherein the metal is a radioisotope of indium (e.g., $^{111}$In); e.g., wherein the metal is a radioisotope of copper (Cu) (e.g., wherein the metal is $^{67}$Cu].

In certain embodiments, the imaging agent comprises $^{99m}$Tc-MIP-1404.

In certain embodiments, the nuclear medicine image is a PET scan.

In certain embodiments, the radionuclide is a radioisotope of a halogen [e.g., a radioisotope of fluorine (e.g., $^{18}$F); e.g., a radioisotope of iodine (e.g., $^{123}$I; e.g., $^{124}$I; e.g., $^{125}$I; e.g., $^{126}$I; e.g., $^{131}$I); e.g., a radioisotope of bromine (e.g., $^{75}$Br; e.g., $^{76}$Br; e.g., $^{77}$Br; e.g., $^{80}$Br; e.g., $^{80m}$Br; e.g., $^{82}$Br; e.g., $^{83}$Br), e.g., a radioisotope of astatine (e.g., $^{211}$At)].

In certain embodiments, the imaging agent comprises [18F]DCFPyL (DCFPyL labeled with $^{18}$F).

In certain embodiments, the radionuclide is a radioisotope of gallium (Ga) (e.g., $^{68}$Ga).

In certain embodiments, the medical images comprise a nuclear medicine image (e.g., a whole-body scan made with a gamma camera) of a first patient following administration to the first patient of an imaging agent comprising a radionuclide (e.g., $^{99m}$Tc)(e.g., wherein the imaging agent comprises $^{99m}$Tc MDP), wherein the instructions cause the processor to automatically analyze the nuclear medicine image by: (a) geographically identifying a boundary (e.g., a 2D boundary; e.g., a 3D boundary) for each of one or more regions of imaged tissue [e.g., organs (e.g., a prostate; e.g., a liver; e.g., lungs or a lung; e.g., lymph nodes), organ structures, sub-organs, organ regions, and/or other regions (e.g., one or more particular bones; e.g., a skeletal region of the patient), e.g., regions of interest] within the nuclear medicine image (e.g., such that portions of the nuclear medicine image falling within and/or outside of the boundaries can be differentiated from each other); and (c) computing (i) a value of each of one or more risk indices and/or (ii) a risk map using the nuclear medicine image with the identified boundaries of the one or more region(s).

In certain embodiments, the instructions cause the processor to, for at least one risk index of the one or more risk indices, compute the value of the risk index by: determining, for each of the one or more regions, a corresponding cancerous tissue level within the region based on intensity values of the nuclear medicine image within the boundary of the region (e.g., by identifying within the nuclear medicine image, a plurality of hotspots within the boundary of the region and computing a total number of and/or a total volume of the identified hotspots); and computing the value of the risk index based on the determined cancerous tissue levels within the one or more regions.

In certain embodiments, the system is a cloud-based system.

In certain embodiments, the processor is a processor of one or more network or Internet host servers.

In another aspect, the invention is directed to a method comprising any one or more of (i) to (v) as follows: (i) receiving and storing, by a processor of a server computing device (e.g., received over a network from a client computing device) medical images [e.g., comprising one or more of the following: targeted PET images, targeted SPECT images, computed tomography (CT) images, magnetic resonance (MR) images, ultrasound (US) images, gamma camera (i.e. scintillation camera) images, and combinations, fusions, or derivatives of any of the above] in a database [e.g., wherein the targeted PET/SPECT/gamma camera image(s) are obtained using one or more radiopharmaceuticals, e.g., [18F]DCFPyL and/or 1404 and/or a composition comprising technetium 99m, e.g., technetium 99m methylenediphosphonate ($^{99m}$Tc MDP), and/or wherein the medical images are obtained using non-radioactive agents or no agents], each medical image associated with a particular patient; (ii) accessing, by the processor, one or more of the medical images and/or related data associated with a particular patient from the database upon user request (e.g., following automated verification that the user is properly credentialed for receiving the requested images and/or data) for transmission to the user for display on a user computing device; (iii) automatically analyzing, by the processor, one or more of the medical images[e.g., to generate a risk map, e.g., a visual representation (e.g., 3D representation) of tissue (e.g., an organ or other part of the body) with graphical denotations (e.g., texture- or color-coding) marking regions of risk of current disease or risk of recurrence of disease, e.g., cancer, e.g., wherein the risk map is displayed as an overlay of the PET/SPECT/CT/MRI/US/combined/derived/fused image of the tissue, or is in place of the image of the tissue]; (iv) generating, by the processor, a radiologist report for a patient according to one or more of the medical images for the patient; and (v) applying, by the processor, a machine learning algorithm to update a process for automatically analyzing one or more of the medical images using accumulated image data in the database, [e.g., wherein the automatically analyzing the one or more medical images in (iii) and/or (v) above comprises any one or more of (a) to (d) as follows: (a) automatically fusing the (e.g., PET, SPECT, CT, MIII, and/or US) image(s) of the tissue; (b) geographically identifying one or more organs, organ structures, sub-organs, organ regions, and/or other regions of the imaged tissue of the patient and production of a 3D image of the geographically identified tissue with PET, SPECT, CT, MM, and/or US data overlaid; (c) computing risk information comprising one or more risk indices, a risk field, or a risk map using data from the database, the image(s) of the tissue, and/or the 3D image in (b); and (d) using the risk information computed in (c) (e.g., and data from the database) to produce a 3D risk picture for the patient].

In certain embodiments, the medical images in the database comprise a series of medical images of a first patient taken over time (e.g., over the course of multiple visits to one or more doctors), and wherein the method comprises determining a value of at least a first risk index for each medical image of the series, thereby tracking determined values of at least the first risk index over time.

In certain embodiments, the receiving and storing of the medical images comprises repeatedly receiving and storing, over time, a plurality of medical images of the first patient, each obtained at a different time (e.g., at a different visit to one or more doctors), to obtain the series of medical images of the first patient.

In certain embodiments, the medical images comprise a single-photon emission computerized tomography (SPECT) scan of a first patient obtained (e.g., to identify one or more hotspots) following administration to the first patient of an imaging agent comprising 1404 labeled with $^{99m}$Tc, and a computed tomography (CT) scan (e.g., to identify anatomical features) of the first patient, wherein the method comprises overlaying the SPECT scan with the CT scan to create a composite image (SPECT-CT) of the first patient.

In certain embodiments, the medical images comprises a positron emission tomography (PET) scan of a first patient obtained following administration to the first patient of an imaging agent comprising [18F]DCFPyL (DCFPyL labeled with $^{18}$F), and a CT scan of the first patient, wherein the method comprises overlaying the PET scan with the CT scan to create a composite image (PET-CT) of the first patient.

In certain embodiments, the medical images comprise a whole-body scan (e.g., including anterior and posterior views) of a first patient made with a gamma camera following administration to the first patient of an imaging agent comprising technetium 99m methylenediphosphonate ($^{99m}$Tc MDP).

In certain embodiments, the medical images comprise a composite image of a first patient, the composite image comprising a CT scan overlaid with a nuclear medicine image (e.g., a SPECT scan; e.g., a PET scan) acquired at substantially the same time and following administration to the first patient of an imaging agent comprising a Prostate Specific Membrane Antigen (PSMA) binding agent comprising a radionuclide, wherein the method comprises automatically analyzing the composite image by: (a) using the composite image to geographically identify a 3D boundary for each of one or more regions of imaged tissue [e.g., organs (e.g., a prostate; e.g., a liver; e.g., lungs or a lung; e.g., lymph nodes), organ structures, sub-organs, organ regions, and/or other regions (e.g., one or more particular bones; e.g., a skeletal region of the patient), e.g., regions of interest] within the nuclear medicine image (e.g., such that portions of the nuclear medicine image falling within and/or outside of the 3D boundaries can be differentiated from each other); and (c) computing (i) a value of each of one or more risk indices and/or a (ii) risk map using the nuclear medicine image with the identified 3D boundaries of the one or more region(s).

In certain embodiments, step (c) comprises, for at least one risk index of the one or more risk indices, computing the value of the risk index by: determining, for each of the one or more regions, a corresponding cancerous tissue level within the region based on intensity values of the nuclear medicine image within the 3D boundary of the region (e.g., by identifying within the nuclear medicine image, a plurality of hotspots within the 3D boundary of the region and computing a total number of and/or a total volume of the identified hotspots); and computing the value of the risk index based on the determined cancerous tissue levels within the one or more regions.

In certain embodiments, the nuclear medicine image is a SPECT scan.

In certain embodiments, the imaging agent comprises a metal chelated to the PSMA binding agent, and wherein the metal is the radionuclide [e.g., wherein the metal is a radioisotope of technetium (Tc) (e.g., wherein the metal is technetium-99m ($^{99m}$Tc)); e.g., wherein the metal is a radioisotope of rhenium (Re) (e.g., wherein the metal is rhenium-188 ($^{188}$Re); e.g., wherein the metal is rhenium-186 ($^{86}$Re)); e.g., wherein the metal is a radioisotope of yttrium (Y) (e.g., wherein the metal is $^{90}$Y); e.g., wherein the metal is a radioisotope of lutetium (Lu)(e.g., wherein the metal is $^{177}$Lu); e.g., wherein the metal is a radioisotope of gallium (Ga) (e.g., wherein the metal is $^{68}$Ga; e.g., wherein the metal is $^{67}$Ga); e.g., wherein the metal is a radioisotope of indium (e.g., $^{111}$In); e.g., wherein the metal is a radioisotope of copper (Cu) (e.g., wherein the metal is $^{67}$Cu)].

In certain embodiments, the imaging agent comprises $^{99m}$Tc-MIP-1404.

In certain embodiments, the nuclear medicine image is a PET scan.

In certain embodiments, the radionuclide is a radioisotope of a halogen [e.g., a radioisotope of fluorine (e.g., $^{18}$F); e.g., a radioisotope of iodine (e.g., $^{123}$I; e.g., $^{124}$I; e.g., $^{125}$I; e.g., $^{126}$I; e.g., $^{131}$I); e.g., a radioisotope of bromine (e.g., $^{75}$Br; e.g., $^{76}$Br; e.g., $^{77}$Br; e.g., $^{80}$Br; e.g., $^{80m}$Br; e.g., $^{82}$Br; e.g., $^{83}$Br), e.g., a radioisotope of astatine (e.g., $^{211}$At)].

In certain embodiments, the imaging agent comprises [18F]DCFPyL (DCFPyL labeled with $^{18}$F).

In certain embodiments, the radionuclide is a radioisotope of gallium (Ga)(e.g., $^{68}$Ga)

In certain embodiments, the medical images comprise a nuclear medicine image (e.g., a whole-body scan made with a gamma camera) of a first patient obtained following administration to the first patient of an imaging agent comprising a radionuclide (e.g., $^{99m}$Tc)(e.g., wherein the imaging agent comprises $^{99m}$Tc MDP), wherein the method comprises automatically analyzing the nuclear medicine image by: (a) geographically identifying a boundary (e.g., a 2D boundary; e.g., a 3D boundary) for each of one or more regions of imaged tissue [e.g., organs (e.g., a prostate; e.g., a liver; e.g., lungs or a lung; e.g., lymph nodes), organ structures, sub-organs, organ regions, and/or other regions (e.g., one or more particular bones; e.g., a skeletal region of the patient), e.g., regions of interest] within the nuclear medicine image (e.g., such that portions of the nuclear medicine image falling within and/or outside of the 3D boundaries can be differentiated from each other); and (c) computing (i) a value of each of one or more risk indices and/or (ii) a risk map using the nuclear medicine image with the identified boundaries of the one or more region(s).

In certain embodiments, step (c) comprises, for at least one risk index of the one or more risk indices, computing the value of the risk index by: determining, for each of the one or more regions, a corresponding cancerous tissue level within the region based on intensity values of the nuclear medicine image within the boundary of the region (e.g., by identifying within the nuclear medicine image, a plurality of hotspots within the 3D boundary of the region and computing a total number of and/or a total volume of the identified hotspots); and computing the value of the risk index based on the determined cancerous tissue levels within the one or more regions.

In certain embodiments, the processor is a processor of a cloud-based system.

In certain embodiments, the processor is a processor of one or more network or Internet host servers.

In another aspect, the invention is directed to a system comprising: a processor (e.g., of a network or Internet host server or of a portable computing device); and a memory having instructions stored thereon, wherein the instructions, when executed by the processor, cause the processor to generate and cause display of an interactive graphical user interface (GUI) element (e.g., cause display of the GUI element on a laptop computer or on a remote computing device, e.g., via a mobile app), the GUI element having user-selectable and/or user-adjustable graphical controls (e.g., slider bars, option buttons, text bars, drop-down boxes, windows, animations, and/or any other GUI widget) for selecting and/or adjusting a digital presentation of a 3D risk picture of a patient for comparison with reference images (e.g., for use in communication of results to patient as a decision-making support) caused to be displayed by the processor (e.g., wherein the reference images displayed to the user or presented for selection by the user are tunable according to one or more predetermined variables associated with the patient, e.g., patient age, time since diagnosis, prior treatment, and/or future treatment).

In certain embodiments, the interactive GUI element is produced from medical images of the patient [e.g., comprising one or more of the following: targeted PET images, targeted SPECT images, magnetic resonance (MR) images, ultrasound (US) images, gamma camera (i.e. scintillation camera) images, and combinations, fusions, or derivatives of any of the above] and/or other images or information (e.g., other images received and stored in the database of the network-based decision support system of any of the aspects and/or embodiments described herein).

In another aspect, the invention is directed to a method for tracking prostate cancer progression and treatment efficacy over time, for one or more patient(s), the method comprising: (a) repeatedly receiving and storing in a database, over time, by a processor of a computing device (e.g., a server computing device), a plurality of medical images for each of the one or more patient(s) to obtain, for each of the one or more patient(s), a series of medical images taken over time (e.g., over the course of multiple visits to one or more doctors); (b) for each of the one or more patient(s), automatically analyzing, by the processor, the series of medical images for the patient to determine values of one or more risk indices [e.g., the values of the one or more risk indices corresponding to numeric values indicative of prostate cancer state and/or progression in the patient (e.g., numeric values identifying a particular cancer stage; e.g., numeric values corresponding to a determined overall survival rate for the patient)] for each medical image of the series, thereby tracking determined values of the one or more risk indices over a course prostate cancer progression and treatment for the patient; and (c) for each of the one or more patient(s), storing, by the processor, the determined values of the one or more risk indices for the patient for further processing and/or causing, by the processor, display of a graphical representation of the determined values of the one or more risk indices for the patient (e.g., causing display of a graph showing variation in the determined values of the one or more risk indices for the patient over time).

In certain embodiments, the series of medical images for a particular patient of the one or more patient(s) comprises: (i) a first image subseries comprising one or more medical images obtained using a first nuclear imaging modality (e.g., SPECT scans; e.g., composite SPECT-CT images) each following administration to the particular patient of a first radiopharmaceutical (e.g., $^{99m}$Tc-MIP-1404) (e.g., wherein the first radiopharmaceutical facilitates imaging of localized disease, e.g., localized prostate cancer); and (ii) a second image subseries comprising one or more medical images obtained using a second nuclear imaging modality (e.g., PET scans; e.g., composite PET-CT images; e.g., whole-body scans) each following administration to the particular patient of a second radiopharmaceutical (e.g., [18F]DCF-PyL; e.g., $^{99m}$Tc MDP) (e.g., wherein the second radiopharmaceutical facilitates imaging of metastatic disease, e.g., metastatic prostate cancer), such that the values of the one or more risk indices determined in step (b) for the particular patient comprise a first subseries of values of a first risk index determined by automated analysis of the first image subseries and a second subseries of values of a second risk index determined by automated analysis of the second image subseries.

In certain embodiments, the medical images of first image subseries are obtained over a first period of time, when prostate cancer of the particular patient is localized (e.g., substantially localized to a prostate of the particular patient), and the medical images of the second image subseries are obtained over a second period of time, when prostate cancer of the particular patient is metastatic (e.g., having spread to regions of the patient outside of the prostate).

In certain embodiments, the first image subseries comprises one or more composite SPECT-CT image(s), each composite SPECT-CT image comprising a CT scan overlaid with a SPECT scan acquired at substantially the same time; the second image subseries comprises one or more composite PET-CT image(s), each composite PET-CT image comprising a CT scan overlaid with a PET scan acquired at substantially the same time; and step (b) comprises: automatically analyzing each of the one or more composite SPECT-CT images by: using the composite SPECT-CT image to geographically identify a 3D boundary of a prostate region (e.g., corresponding to a prostate of the patient) within the SPECT scan of the composite SPECT-CT image (e.g., such that portions of the nuclear medicine image falling within and/or outside of the 3D boundary of the prostate region can be differentiated from each other); and computing a value of the first risk index using the SPECT scan with the identified 3D boundary of the prostate region (e.g., computed based on a region of the SPECT scan corresponding to the identified 3D boundary of the prostate region); and automatically analyzing each of the one or more composite PET-CT images by: using the composite PET-CT image to geographically identify a 3D boundary of one or more metastatic regions within the PET scan of the composite PET-CT image, the one or metastatic regions including regions corresponding to patient tissue locations outside of the prostate [e.g., organs (e.g., a prostate; e.g., a liver; e.g., lungs or a lung; e.g., lymph nodes), organ structures, sub-organs, organ regions, and/or other regions (e.g., one or more particular bones; e.g., a skeletal region corresponding to the patient's skeleton), e.g., regions of interest] (e.g., such that portions of the PET imaging scan falling within and/or outside of the 3D boundaries of the one or more metastatic region(s) can be differentiated from each other); and computing a value of the second risk index using the PET scan with the identified 3D boundaries of the one or more metastatic region(s).

In certain embodiments, the first image subseries comprises one or more composite SPECT-CT image(s), each composite SPECT-CT image comprising a CT scan overlaid with a SPECT scan acquired at substantially the same time; the second image subseries comprises one or more whole-body scan(s); and step (b) comprises: automatically analyzing each of the one or more composite SPECT-CT images by: using the composite SPECT-CT image to geographically identify a 3D boundary of a prostate region (e.g., corresponding to a prostate of the patient) within the SPECT scan of the composite SPECT-CT image (e.g., such that portions of the nuclear medicine image falling within and/or outside of the 3D boundary of the prostate region can be differentiated from each other); and computing a value of the first risk index using the SPECT scan with the identified 3D boundary of the prostate region (e.g., computed based on a region of the SPECT scan corresponding to the identified 3D boundary of the prostate region); and automatically analyzing each of the one or more whole-body scan(s) by: geographically identifying a boundary of one or more metastatic regions within the whole-body scan, the one or metastatic regions including regions corresponding to patient tissue locations outside of the prostate [(e.g., one or more particular bones; e.g., a skeletal region corresponding to the patient's skeleton), e.g., regions of interest] (e.g., such that portions of the whole-body scan falling within and/or outside of the boundaries of the one or more metastatic region(s) can be differentiated from each other); and computing a value of the second risk index using the PET scan with the identified 3D boundaries of the one or more metastatic region(s).

In another aspect, the invention is directed to a system for tracking prostate cancer progression and treatment efficacy over time, for one or more patient(s), the system comprising: a processor (e.g., of a network or Internet host server); and a memory having instructions stored thereon, wherein the instructions, when executed by the processor, cause the processor to: (a) repeatedly receive and store in a database, over time, a plurality of medical images for each of the one or more patient(s) to obtain, for each of the one or more patient(s), a series of medical images taken over time (e.g., over the course of multiple visits to one or more doctors); (b) for each of the one or more patient(s), automatically analyze the series of medical images for the patient to determine values of one or more risk indices [e.g., the values of the one or more risk indices corresponding to numeric values indicative of prostate cancer state and/or progression in the patient (e.g., numeric values identifying a particular cancer stage; e.g., numeric values corresponding to a determined overall survival rate for the patient)] for each medical image of the series, thereby tracking determined values of the one or more risk indices over a course prostate cancer progression and treatment for the patient; and (c) for each of the one or more patient(s), store the determined values of the one or more risk indices for the patient for further processing and/or cause display of a graphical representation of the determined values of the one or more risk indices for the patient (e.g., causing display of a graph showing variation in the determined values of the one or more risk indices for the patient over time).

In certain embodiments, the series of medical images for a particular patient of the one or more patient(s) comprises: (i) a first image subseries comprising one or more medical images obtained using a first nuclear imaging modality (e.g., SPECT scans; e.g., composite SPECT-CT images) each following administration to the particular patient of a first radiopharmaceutical (e.g., $^{99m}$Tc-MIP-1404) (e.g., wherein the first radiopharmaceutical facilitates imaging of localized disease, e.g., localized prostate cancer); and (ii) a second image subseries comprising one or more medical images obtained using a second nuclear imaging modality (e.g., PET scans; e.g., composite PET-CT images; e.g., whole-body scans) each following administration to the particular patient of a second radiopharmaceutical (e.g., [18F]DCF-PyL; e.g., $^{99m}$Tc MDP) (e.g., wherein the second radiopharmaceutical facilitates imaging of metastatic disease, e.g., metastatic prostate cancer), such that the values of the one or more risk indices determined in step (b) for the particular patient comprise a first subseries of values of a first risk index determined by automated analysis of the first image subseries and a second subseries of values of a second risk index determined by automated analysis of the second image subseries.

In certain embodiments, the medical images of first image subseries are obtained over a first period of time, when prostate cancer of the particular patient is localized (e.g., substantially localized to a prostate of the particular patient), and the medical images of the second image subseries are obtained over a second period of time, when prostate cancer of the particular patient is metastatic (e.g., having spread to regions of the patient outside of the prostate).

In certain embodiments, the first image subseries comprises one or more composite SPECT-CT image(s), each composite SPECT-CT image comprising a CT scan overlaid with a SPECT scan acquired at substantially the same time; the second image subseries comprises one or more composite PET-CT image(s), each composite PET-CT image comprising a CT scan overlaid with a PET scan acquired at substantially the same time; and the instructions cause the processor to, at step (b): automatically analyze each of the one or more composite SPECT-CT images by: using the composite SPECT-CT image to geographically identify a 3D boundary of a prostate region (e.g., corresponding to a prostate of the patient) within the SPECT scan of the composite SPECT-CT image (e.g., such that portions of the nuclear medicine image falling within and/or outside of the 3D boundary of the prostate region can be differentiated from each other); and computing a value of the first risk index using the SPECT scan with the identified 3D boundary of the prostate region (e.g., computed based on a region of the SPECT scan corresponding to the identified 3D boundary of the prostate region); and automatically analyze each of the one or more composite PET-CT images by: using the composite PET-CT image to geographically identify a 3D boundary of one or more metastatic regions within the PET scan of the composite PET-CT image, the one or metastatic regions including regions corresponding to patient tissue locations outside of the prostate [e.g., organs (e.g., a prostate; e.g., a liver; e.g., lungs or a lung; e.g., lymph nodes), organ structures, sub-organs, organ regions, and/or other regions (e.g., one or more particular bones; e.g., a skeletal region corresponding to the patient's skeleton), e.g., regions of interest] (e.g., such that portions of the PET imaging scan falling within and/or outside of the 3D boundaries of the one or more metastatic region(s) can be differentiated from each other); and computing a value of the second risk index using the PET scan with the identified 3D boundaries of the one or more metastatic region(s).

In certain embodiments, the first image subseries comprises one or more composite SPECT-CT image(s), each composite SPECT-CT image comprising a CT scan overlaid with a SPECT scan acquired at substantially the same time; the second image subseries comprises one or more whole-body scan(s); and the instructions cause the processor to, at step (b): automatically analyze each of the one or more composite SPECT-CT images by: using the composite SPECT-CT image to geographically identify a 3D boundary of a prostate region (e.g., corresponding to a prostate of the patient) within the SPECT scan of the composite SPECT-CT image (e.g., such that portions of the nuclear medicine image falling within and/or outside of the 3D boundary of the prostate region can be differentiated from each other); and computing a value of the first risk index using the SPECT scan with the identified 3D boundary of the prostate region (e.g., computed based on a region of the SPECT scan corresponding to the identified 3D boundary of the prostate region); and automatically analyze each of the one or more whole-body scan(s) by: geographically identifying a boundary of one or more metastatic regions within the whole-body scan, the one or metastatic regions including regions corresponding to patient tissue locations outside of the prostate [(e.g., one or more particular bones; e.g., a skeletal region corresponding to the patient's skeleton), e.g., regions of interest] (e.g., such that portions of the whole-body scan falling within and/or outside of the boundaries of the one or more metastatic region(s) can be differentiated from each other); and computing a value of the second risk index using the PET scan with the identified 3D boundaries of the one or more metastatic region(s).

Embodiments described with respect to one aspect of the invention may be, applied to another aspect of the invention (e.g., features of embodiments described with respect to one independent claim, e.g., a method claim, are contemplated to be applicable to other embodiments of other independent claims, e.g., a system claim, and vice versa).

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 3 is a screenshot of a GUI window in the BSI Cloud application (displayed to a user) that allows a user to enter information about a patient and upload and/or access medical images for the patient, e.g., series of images obtained over a period of time, according to an illustrative embodiment.

FIG. 6 is a block diagram showing a set of functionalities offered by the a cloud-based platform and supported graphical user interface (GUI) decision-making tools described herein, according to an illustrative embodiment.

Figure 1:
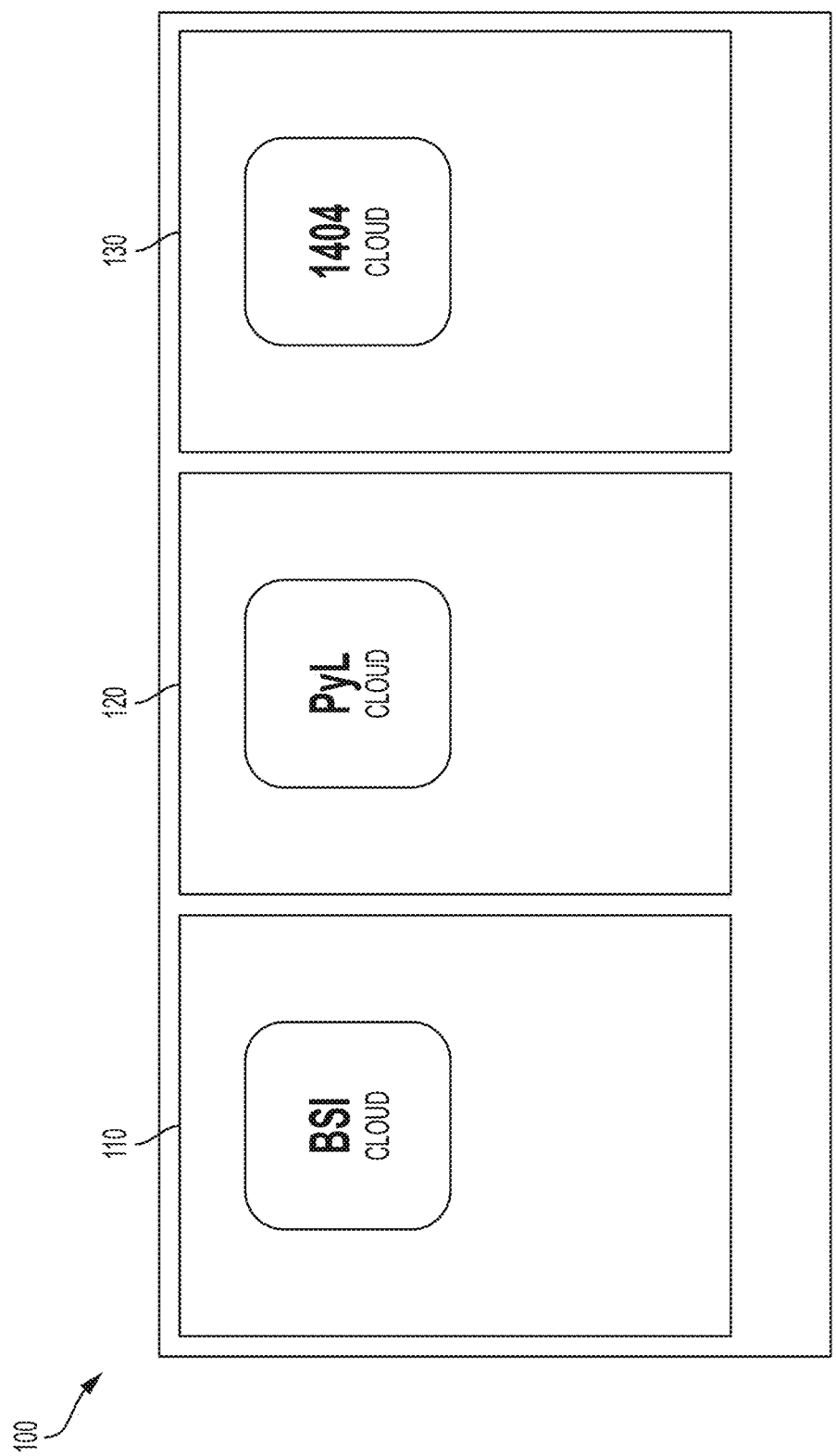
FIG. 1 is a screenshot of a graphical user interface (GUI) showing mobile app icons for three cloud-based services, according to illustrative embodiments.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

A. Medical Imaging Modalities, Associated Radiopharmaceuticals, and Computed Risk Indices FIG. 1 shows mobile app icons 100 for three cloud-based services, according to illustrative embodiments. As described in the following, the cloud-based services of the platform described herein provide for processing and analysis of medical images in a fully automated fashion and/or in combination with a user interaction (e.g., in a semi-automated fashion). The medical images include nuclear medicine images, obtained using a nuclear imaging modality such as whole-body scans with a gamma camera, Positron Emission Tomography (PET) scans, and Single-Photon Emission Tomography (SPECT) scans.

In certain embodiments, nuclear medicine images use imaging agents comprising radiopharmaceuticals. Nuclear medicine images are obtained following administration of a radiopharmaceutical to a patient, and provide information regarding the distribution of the radiopharmaceutical within the patient. Radiopharmaceuticals are compounds that comprise a radionuclide.

As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Nuclear medicine images (e.g., PET scans; e.g., SPECT scans; e.g., whole-body scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. As described in the following, risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example $^{18}$F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. As described in the following, risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties.

A.i PET Imaging Radionuclide Labelled PSMA Binding Agents

In certain embodiments, the radionuclide labelled PSMA binding agent is a radionuclide labelled PSMA binding agent appropriate for PET imaging.

In certain embodiments, the radionuclide labelled PSMA binding agent comprises [18F]DCFPyL (also referred to as PyL™; also referred to as DCFPyL-18F):

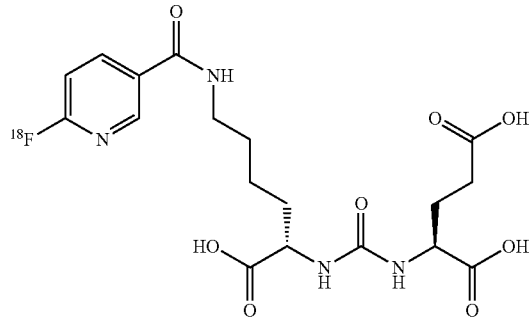 [SMILES: O=C(O)CC[C@H](NC(=O)N[C@@H](CCCCNC(=O)c1ccc([18F])nc1)C(=O)O)C(=O)O]

[18F]DCFPyL,
or a pharmaceutically acceptable salt thereof.

In certain embodiments, the radionuclide labelled PSMA binding agent comprises [18F]DCFBC:

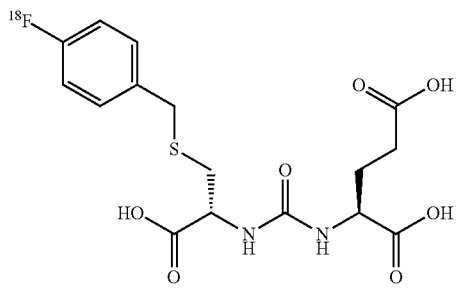 [SMILES: O=C(O)CC[C@H](NC(=O)N[C@@H](CSCc1ccc([18F])cc1)C(=O)O)C(=O)O]

[18F]DCFBC,
or a pharmaceutically acceptable salt thereof.

In certain embodiments, the radionuclide labelled PSMA binding agent comprises $^{68}$Ga-PSMA-HBED-CC (also referred to as $^{68}$Ga-PSMA-11):

$^{68}$Ga-PSMA-HBED-CC,
or a pharmaceutically acceptable salt thereof.

In certain embodiments, the radionuclide labelled PSMA binding agent comprises PSMA-617:

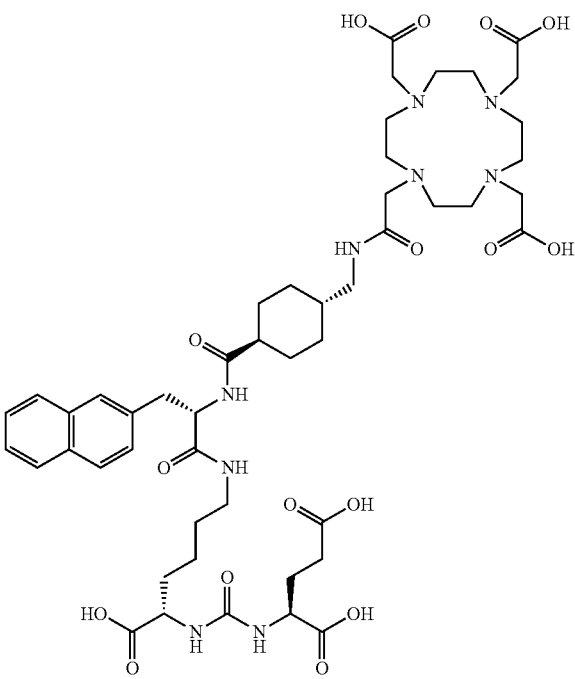

PSMA-617,
or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, the radionuclide labelled PSMA binding agent comprises $^{177}$Lu-PSMA-617, which is PSMA-617 labelled with $^{177}$Lu, or a pharmaceutically acceptable salt thereof.

In certain embodiments, the radionuclide labelled PSMA binding agent comprises PSMA-I&T:

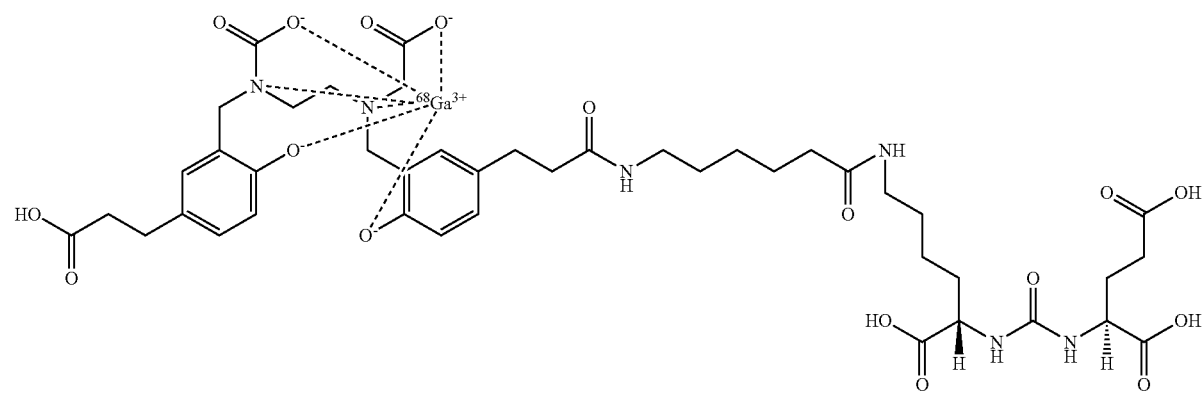

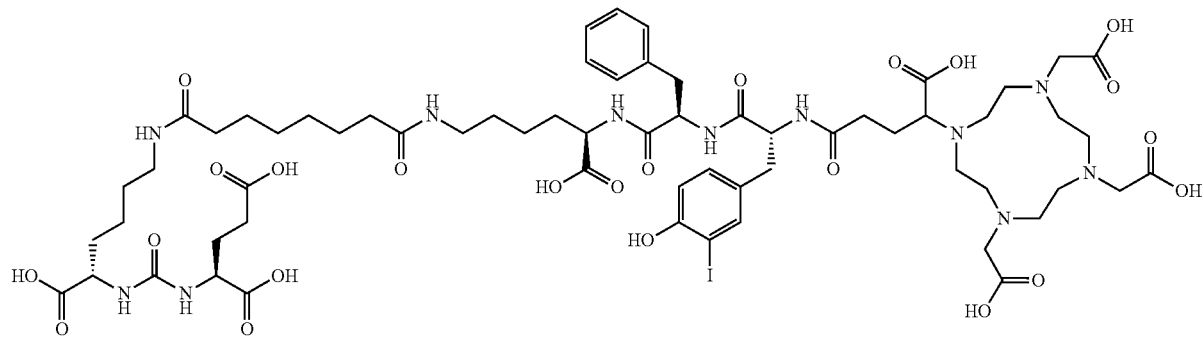 [SMILES: O=C(O)CC[C@H](NC(=O)N[C@@H](CCCCNC(=O)CCCCCCC(=O)NCCCC[C@@H](NC(=O)[C@@H](Cc1ccccc1)NC(=O)[C@@H](Cc1ccc(O)c(I)c1)NC(=O)CCC(C(=O)O)N1CCN(CC(=O)O)CCN(CC(=O)O)CCN(CC(=O)O)CC1)C(=O)O)C(=O)O)C(=O)O]

PSMA-I&T, or a pharmaceutically acceptable salt thereof. In certain embodiments, the radionuclide labelled PSMA binding agent comprises $^{68}$Ga-PSMA-I&T, which is PSMA-I&T labelled with $^{68}$Ga, or a pharmaceutically acceptable salt thereof.

In certain embodiments, the radionuclide labelled PSMA binding agent comprises PSMA-1007:

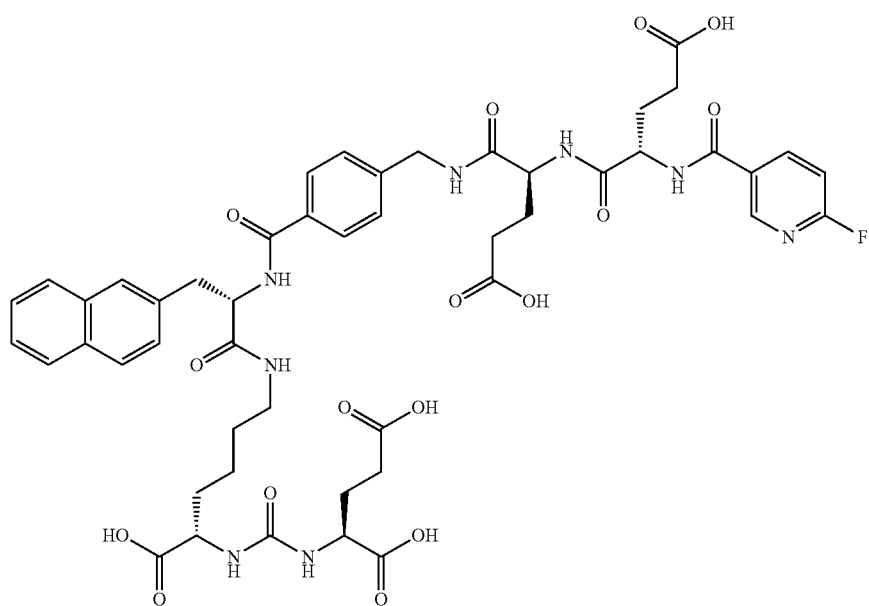 [SMILES: O=C(O)CC[C@H](NC(=O)N[C@@H](CCCCNC(=O)[C@H](Cc1ccc2ccccc2c1)NC(=O)c1ccc(CNC(=O)[C@H](CCC(=O)O)NC(=O)[C@H](CCC(=O)O)NC(=O)c2ccc(F)nc2)cc1)C(=O)O)C(=O)O]

PSMA-1007, or a pharmaceutically acceptable salt thereof. In certain embodiments, the radionuclide labelled PSMA binding agent comprises $^{18}$F-PSMA-1007, which is PSMA-1007 labelled with $^{18}$F, or a pharmaceutically acceptable salt thereof.

A.ii SPECT Imaging Radionuclide Labelled PSMA Binding Agents

In certain embodiments, the radionuclide labelled PSMA binding agent is a radionuclide labelled PSMA binding agent appropriate for SPECT imaging.

In certain embodiments, the radionuclide labelled PSMA binding agent comprises 1404 (also referred to as MIP-1404):

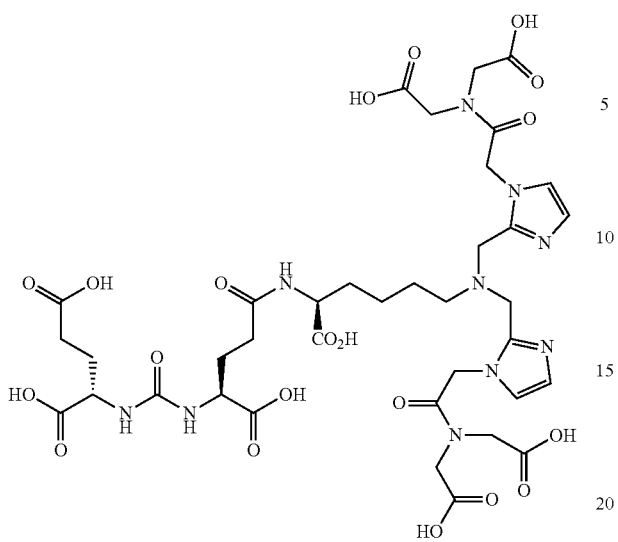

1404,
or a pharmaceutically acceptable salt thereof.

In certain embodiments, the radionuclide labelled PSMA binding agent comprises 1405 (also referred to as MIP-1405):

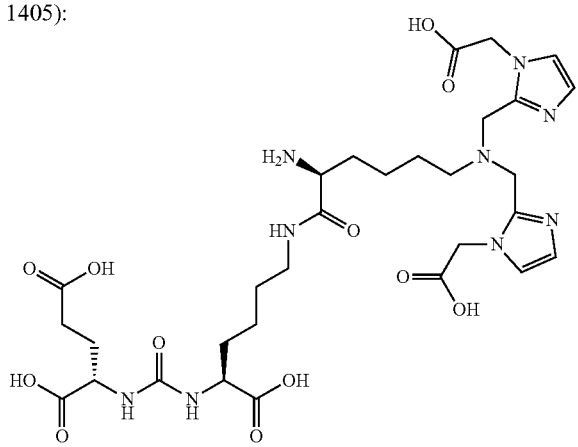

1405,
or a pharmaceutically acceptable salt thereof.

In certain embodiments, the radionuclide labelled PSMA binding agent comprises 1427 (also referred to as MIP-1427):

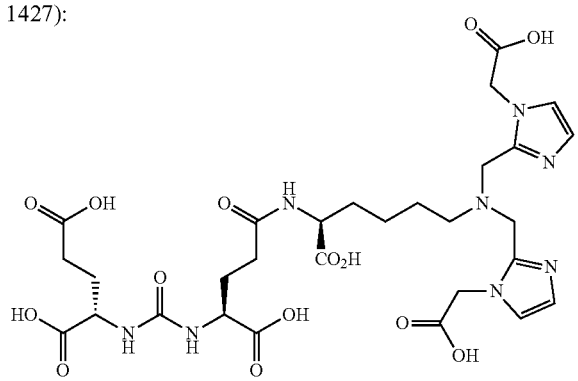

1427,
or a pharmaceutically acceptable salt thereof.

In certain embodiments, the radionuclide labelled PSMA binding agent comprises 1428 (also referred to as MIP-1428):

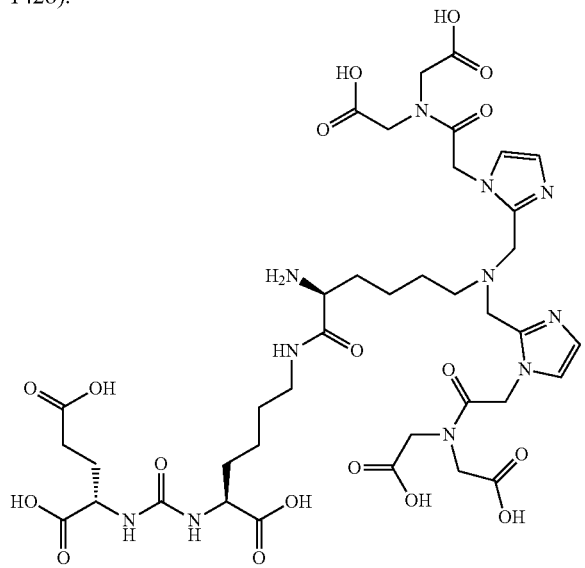

1428,
or a pharmaceutically acceptable salt thereof.

In certain embodiments, the PSMA binding agent is labelled with a radionuclide by chelating it to a radioisotope of a metal [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)].

In certain embodiments, 1404 is labelled with a radionuclide (e.g., chelated to a radioisotope of a metal). In certain embodiments, the radionuclide labelled PSMA binding agent comprises $^{99m}$Tc-MIP-1404, which is 1404 labelled with (e.g., chelated to)$^{99m}$Tc:

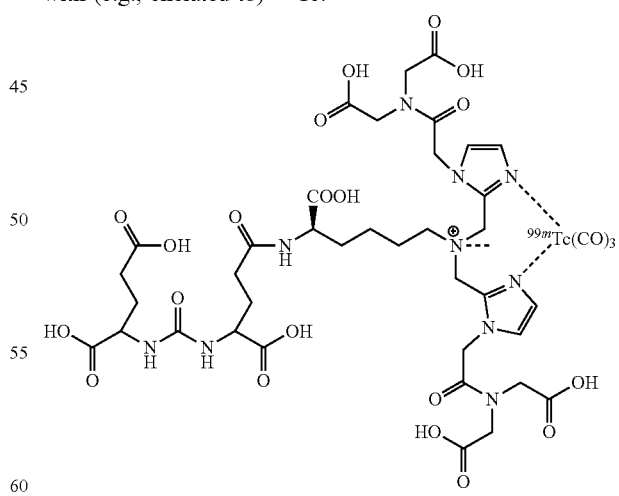

$^{99m}$Tc-MIP-1404,
or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1404, with the other metal radioisotope substituted for $^{99m}$Tc.

In certain embodiments, 1405 is labelled with a radionuclide (e.g., chelated to a radioisotope of a metal). In certain embodiments, the radionuclide labelled PSMA binding agent comprises $^{99m}$Tc-MIP-1405, which is 1405 labelled with (e.g., chelated to)$^{99m}$Tc:

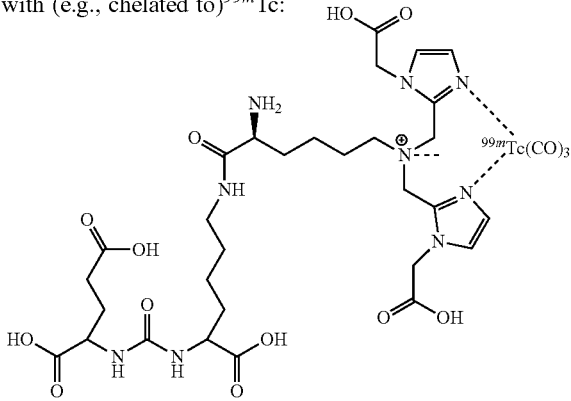

$^{99m}$Tc-MIP-1405, or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu) (e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1405, with the other metal radioisotope substituted for $^{99m}$Tc.

In certain embodiments, 1427 is labelled with (e.g., chelated to) a radioisotope of a metal, to form a compound according to the formula below:

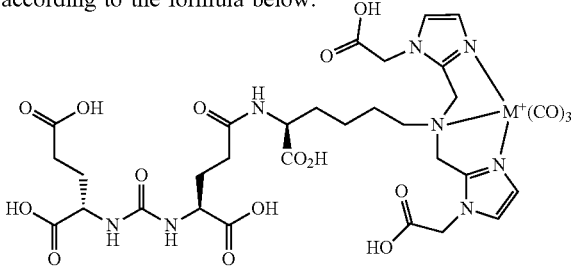

1427 chelated to a metal, or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., In); e.g., a radioisotope of copper (Cu) (e.g., $^{67}$Cu)] with which 1427 is labelled.

In certain embodiments, 1428 is labelled with (e.g., chelated to) a radioisotope of a metal, to form a compound according to the formula below:

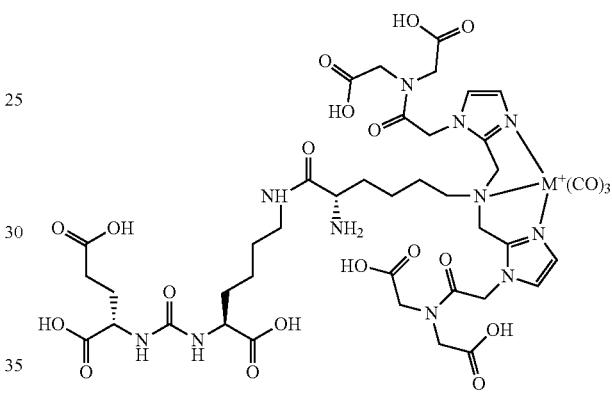

1428 chelated to a metal, or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., In); e.g., a radioisotope of copper (Cu) (e.g., $^{67}$Cu)] with which 1428 is labelled.

In certain embodiments, the radionuclide labelled PSMA binding agent comprises PSMA I&S:

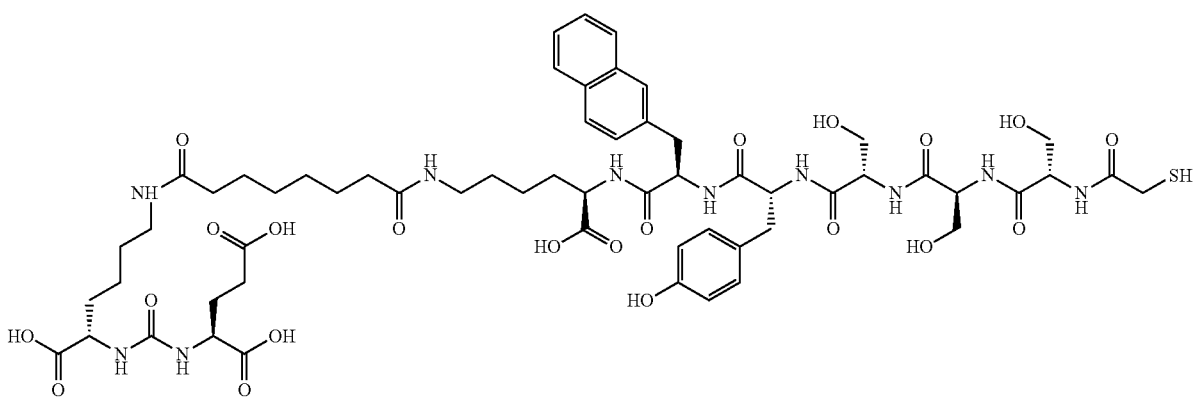 [SMILES: O=C(O)CC[C@H](NC(=O)N[C@@H](CCCCNC(=O)CCCCCCC(=O)NCCCC[C@@H](NC(=O)[C@@H](Cc1ccc2ccccc2c1)NC(=O)[C@@H](Cc1ccc(O)cc1)NC(=O)[C@H](CO)NC(=O)[C@H](CO)NC(=O)[C@H](CO)NC(=O)CS)C(=O)O)C(=O)O)C(=O)O]

PSMA I& S, or a pharmaceutically acceptable salt thereof. In certain embodiments, the radionuclide labelled PSMA binding agent comprises $^{99m}$Tc-PSMA I&S, which is PSMA I&S labelled with $^{99m}$Tc, or a pharmaceutically acceptable salt thereof.

A.iii Whole-Body Bone Scans

Turning to FIG. 1, BSI Cloud 130 refers to a cloud-based decision support system that implements BSI values. BSI refers to bone scan index, which is a value computed from a method for detecting skeletal lesions from whole-body scanning (and anterior and posterior views) with a gamma camera following administration of the radionuclide technetium 99m methylenediphosphonate ($^{99m}$Tc MDP). Further explanation of BSI is provided, for example, in U.S. Pat. No. 8,855,387, which is incorporated herein by reference in its entirety, as well as in U.S. patent application Ser. No. 15/282,422, filed Sep. 30, 2016, which is incorporated herein by reference in its entirety.

In particular, BSI is computed from whole-body scans by segmenting anterior and posterior views of the whole-body scan of the patient to geographically identify boundaries of regions within the views that correspond to various portions of the patient's skeleton. Segmentation of the patient's skeleton can be performed using a variety of approaches, such as the Active Shape Model-based approach and the atlas image registration approach (which registers the anterior and posterior views of a whole body scan with reference anterior and posterior views of a reference whole body scan that have already been segmented (referred to as an atlas image)) described in U.S. Pat. No. 8,855,387. Other approaches, based on machine learning techniques (e.g., artificial neural networks (ANNs); e.g., convolutional neural networks (CNNs)) may also be used.

The BSI value is computed based on the intensity values of whole-body scan within the identified boundaries of the various skeletal regions. As discussed above, hotspots that correspond to localized regions of high intensity within the views (anterior and/or posterior views) of the whole-body scan can be detected. Hotspots may be detected and/or classified as corresponding to cancerous lesions (e.g., metastases) using a variety of approaches, including, as described in U.S. Pat. No. 8,855,387, machine learning techniques such as ANNs.

Hotspots corresponding to cancerous tissue lesions within the patient's skeleton, once detected, can be used to determine a risk index that provides a measure of disease state for the patient. For example, cancerous tissue levels within one or more regions, such as particular bones and/or the overall skeletal region, can be determined based on features of detected hotspots (e.g., detected hotspots classified as metastases). For example, a cancerous tissue level within a region (e.g., a particular bone; e.g., the overall skeletal region) may be determined based on (e.g., as a function of) a total number of detected hotspots within the region, a total volume of detected hotspots within the region, an average intensity of detected hotspots, a maximal intensity of detected hotspots, and the like, as well as combinations thereof. Properties of the one or more regions, such as their area or volume may also be used. For example, a total number and/or total volume of detected hotspots may be normalized (e.g., divided) by a volume and/or area of the region in which they are detected. A risk index may be determined based on the determined cancerous tissue levels within one or more regions, directly, e.g., as the cancerous tissue level within a single region, or determined from cancerous tissue levels in multiple regions (e.g., as an average; e.g., as a scaled sum; e.g., as a ratio; etc.), or even using machine learning approaches.

For example, the BSI value is a risk index that is a numeric value that quantifies the fraction of the total skeleton of the patient that is involved by cancerous tissue (e.g., tumors), based on the detected hotspots. The BSI value can be compared between different patients, and used as an objective measure of disease state and risk for a particular patient. Notably, since BSI is computed in an automated fashion, variability due to human factors such as radiologist interpretation of images is avoided.

Moreover, a variety of actionable information can be obtained from a patient's BSI value. For example, BSI can be correlated with prognostic values that provide a measure of disease state, progression, life expectancy (e.g., overall survival), treatment efficacy, and the like for the patient. Accordingly, a patient's BSI value can be used and tracked over time (e.g., over the course of multiple visits to one or more doctors) to provide them or their physician with an objective metric of what state their cancer is in, how fast it is progressing, what their outlook is, and whether one or more particular treatments are proving effective.

A.iv Positron Emission Tomography (PET) Scans

PyL Cloud 120 refers to a cloud-based system that uses medical images obtained with the agent PyL™, which is DCFPyL labeled with $^{18}$F ([18F]DCFPyL). The patient, after injection of the imaging agent, receives a positron emission tomography (PET) scan to identify hot spots, and a CT scan. Further information about the PyL™ imaging agent is provided above, and, for example, in U.S. Pat. No. 8,778,305, which is incorporated herein by reference in its entirety.

In certain embodiments, the PET scan and the CT scan are combined as a composite image comprising the CT scan overlaid with the PET scan. As used herein, overlaying one image (e.g., a CT scan) with another (e.g., a PET scan) refers to establishing a mapping between coordinates and/or pixels or voxels of the two images that that represent the same physical locations (e.g., within the patient). CT scans provide accurate anatomical information in the form of detailed three-dimensional (3D) images of internal organs, bones, soft tissue, and blood vessels. Accordingly, 3D boundaries of specific regions of imaged tissue can be accurately identified by analysis of CT scans. For example, automated segmentation of CT scans can be performed to identify 3D boundaries of specific organs (e.g., a prostate, lymph nodes, a lung or lungs), sub-organs, organ regions, as well as other regions of imaged tissue, such as particular bones and an overall skeletal region of the patient. Automated segmentation of CT scans can be accomplished via a variety of approaches, include machine learning techniques [e.g., ANN-based approaches (including, e.g., convolutional neural networks (CNNs)], atlas image registration, and combinations thereof. In certain embodiments, manual segmentation of CT images can also be utilized, alone or in combination with automated segmentation approaches (e.g., to refine 3D boundaries identified via automated segmentation; e.g., to provide an initial starting point for an automated segmentation approach).

Once the 3D boundaries of various regions are identified within a CT scan of a composite image, by virtue of the mapping between the CT scan and PET scan of the composite image, the identified 3D boundaries can be transferred to the PET image. Accordingly, regions of the PET image falling within and/or outside of the identified 3D boundaries can be accurately identified.

In certain embodiments, composite images comprising CT scans overlaid with PET scans are obtained using dedicated PET-CT scanner instruments common in many hospitals, and are uploaded as medical images to the cloud-based platform described herein. In certain embodiments, a PET scan and a corresponding CT scan are obtained separately (but at substantially the same time), and uploaded to the cloud-based platform described herein. In such cases, the separately obtained PET and CT scans can be automatically fused to create a composite image.

In certain embodiments, once the 3D boundaries of the various regions are identified within the PET scan, one or more risk indices can be computed in a similar fashion to that described above with regard to BSI. In particular, in certain embodiments, intensity values of the PET scan in relation to (e.g., within and/or outside of) the 3D boundaries of the identified regions can be used to determine levels of cancerous tissue within the identified regions, e.g., based on features of detected hotspots (e.g., detected hotspots corresponding to metastases). Risk indices can then be computed based on the determined cancerous tissue levels. For example, hotspots within the PET scan can be identified, and, based on features such as their size, number, and distribution with respect to the identified regions, used to compute one or more risk indices. As with BSI, risk indices determined from PET scans can be correlated with prognostic values and tracked over time (e.g., over the course of multiple visits to one or more doctors) to provide patients or their physician with an objective metric of what state their cancer is in, how fast it is progressing, what their outlook is, and whether one or more particular treatments are proving effective. The approaches described herein with regard to PET imaging using PyL™ as a radiopharmaceutical can be applied to a variety of other radiopharmaceuticals, such as those described above, including, without limitation NaF, radioisotopes of choline, and any of the PSMA binding agents described in section A.i above.

A.v Single-Photon Emission Computerized Tomography (SPECT) Scans

1404 Cloud 130 refers to a cloud-based system that uses medical images obtained with the agent $^{99m}$Tc-MIP-1404, which, as described above, is 1404 labeled with $Tc^{99m}$. After injection of the imaging agent, the patient receives a single-photon emission computerized tomography (SPECT) scan, e.g., to identify hot spots, and a computed tomography (CT) scan, e.g., to identify anatomical features. These images are overlaid to make a composite image (SPECT/CT). Further information about $^{99m}$Tc-MIP-1404 imaging agent is provided above, and, for example, in U.S. Pat. Nos. 8,211,401 and 8,962,799, both of which are incorporated herein by reference in their entireties.

SPECT and CT scans can be analyzed in a manner similar to that described above with respect to PET and CT scans, in order to determine one or more risk indices. In particular, as with PET and CT scans, the SPECT scan and the CT scan can be combined in a composite image in which the CT scan is overlaid with the SPECT scan—a composite SPECT-CT image. As with composite PET-CT images, composite SPECT-CT images may be directly received as medical images by the cloud-based platform described herein (e.g., having been obtained via dedicated SPECT-CT imager in a hospital), or may be created by the cloud-based platform following receipt of separate SPECT scans and CT scans.

Figure 2:
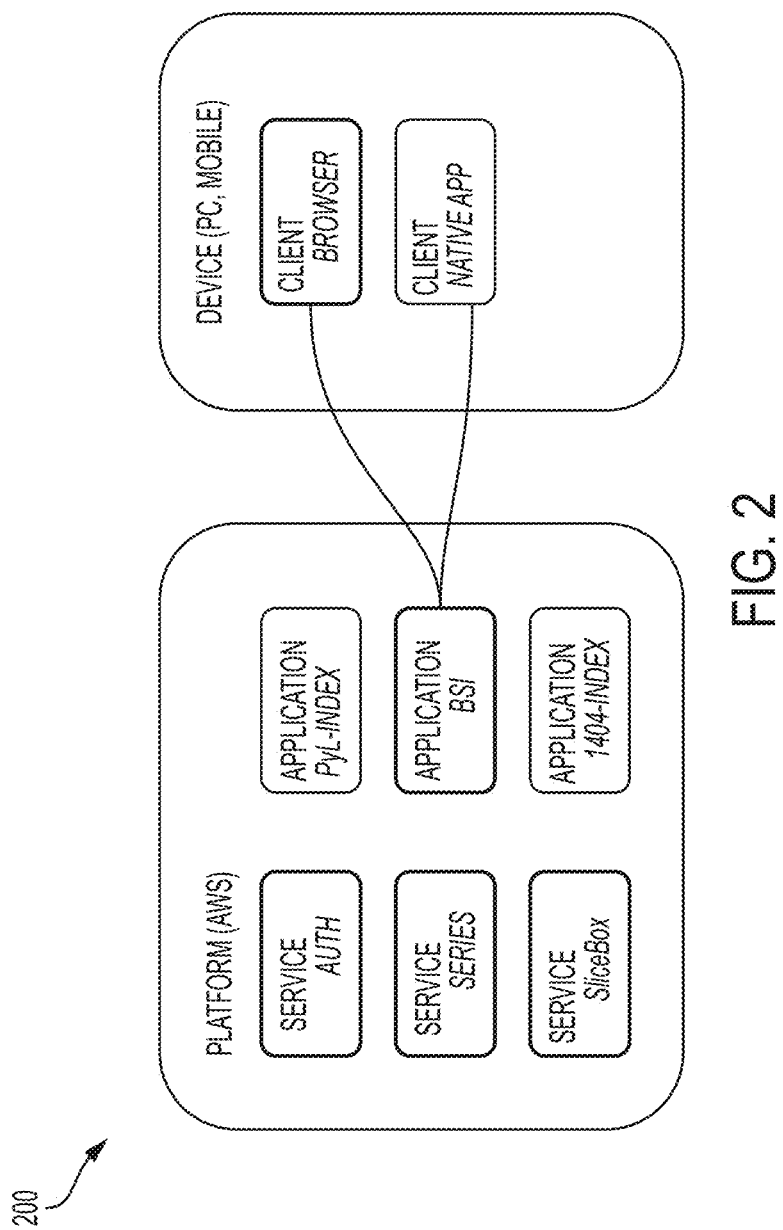
FIG. 2 is a schematic showing the relationship between a platform and a computing device (e.g., personal computer or mobile computing device, e.g., smart phone) running an application, according to illustrative embodiments of the invention.

Similar to PET-CT images, 3D boundaries of various regions of imaged tissue can be identified within the SPECT image by virtue of the overlay with the CT image of the composite image. Intensity variations within the SPECT image, in relation to the 3D boundaries can be used to compute one or more risk indices. As with the approaches for computing risk indices from composite PET-CT images, this may comprise determine levels of cancerous tissue within the identified regions, for example by detecting hotspots within the 3D boundaries of the identified regions. Such risk indices can be correlated with prognostic values and tracked over time (e.g., over the course of multiple visits to one or more doctors) to provide patients or their physician with an objective metric of what state their cancer is in, how fast it is progressing, what their outlook is, and whether one or more particular treatments are proving effective. The approaches described herein with regard to SPECT imaging using $^{99m}$Tc-MIP-1404 as a radiopharmaceutical can be applied to a variety of other radiopharmaceuticals, such as those described above, including, without limitation, any of the PSMA binding agents described in section A.ii above B. Platform Services and Computing Device Components FIG. 2 is a schematic 200 showing the relationship between a platform and a computing device (e.g., personal computer or mobile computing device, e.g., smart phone) running an application, according to illustrative embodiments of the invention. The platform performs various services, for example, user authentication ("Auth"), image and other data storage ("SliceBox), and the like—many more services than those shown may be provided. The applications may have both a platform component and a device component (e.g., native app on the client device).

Figure 9:
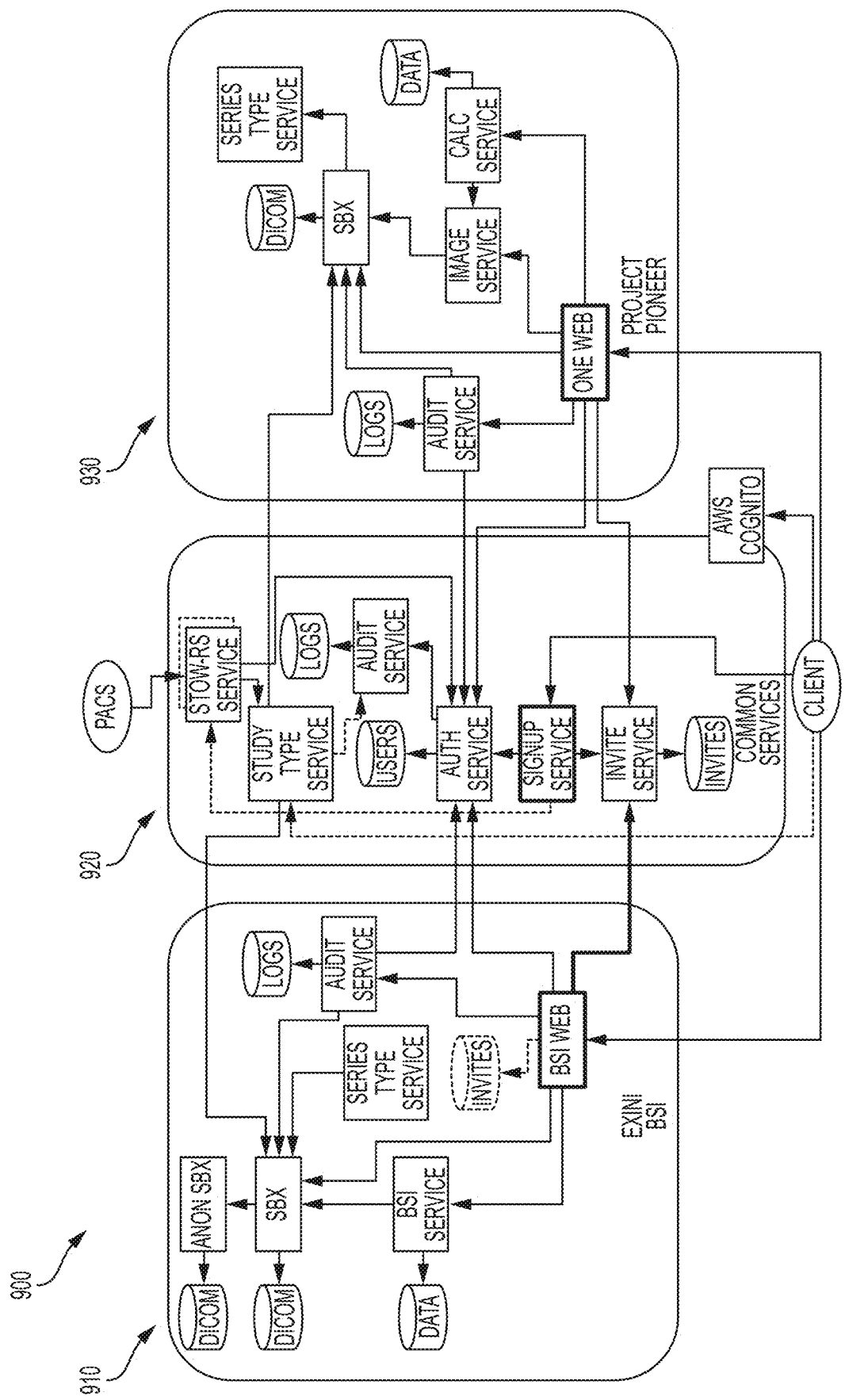
FIG. 9 is block diagram of an example architecture for implementing the cloud based platform described herein, according to an illustrative embodiment.

FIG. 9 shows an example architecture 900 for implementing the cloud-based platform described herein, and providing various services such as the BSI Cloud, PyL Cloud, and 1404 Cloud services described above. The architecture shown in FIG. 9 can be used to implement the platform described herein on a variety of datacenters, including publicly available datacenters. The datacenter provides infrastructure in the form of servers and networks and provides services for e.g. networking, messaging, authentication, logging and storage. The architecture 900 for the platform uses a series of functional units with limited scope referred to as microservices. Each microservice handles an isolated set of tasks such as image storage, calculation of a risk index, identification of medical image type, and other tasks. Services (e.g., microservices) can communicate with each other using standard protocols such as Hypertext Transfer Protocol (HTTP). Organizing the platform into a network of microservices, as shown in the architecture 900 of FIG. 9, allows for parts of the platform to be scaled individually to meet high demand and to ensure minimal downtime.

In certain embodiments, such an architecture allows for components to be improved or replaced without affecting other parts of the platform. The example architecture 900 shown in FIG. 9 includes a set 920 of microservices that that are common to two or more applications in the platform. The left 910 and right 930 panels show microservices in two applications. The microservice network shown in the left panel 910 implements a version of the BSI Cloud service, as described above, and provides for calculation of an automated BSI index (aBSI), which is a risk index derived from automated analysis of whole-body scans obtained with a gamma camera. The microservice network shown in the right panel 930 implements a version of the 1404 Cloud service, as described above, and provides for automated calculation of a SPECT index, which is a risk index derived from automated analysis of composite SPECT-CT images.

C. Image Collection, Analysis, and Result Presentation

Figure 3:
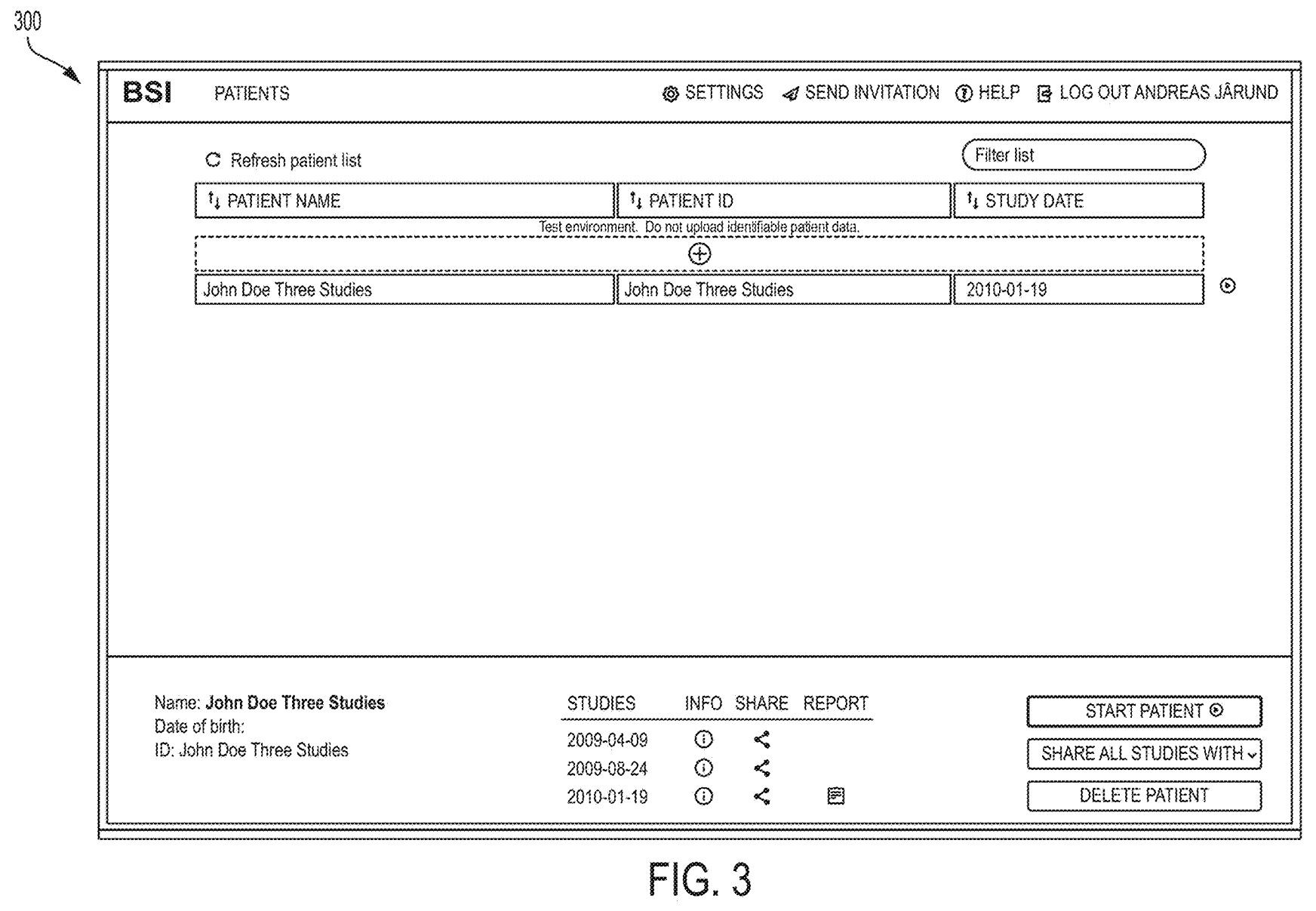

FIG. 3 is a GUI window 300 in the BSI Cloud application (displayed to a user) that allows a user to enter information about a patient and upload and/or access medical images for the patient, e.g., series of images obtained over a period of time.

Figure 4:
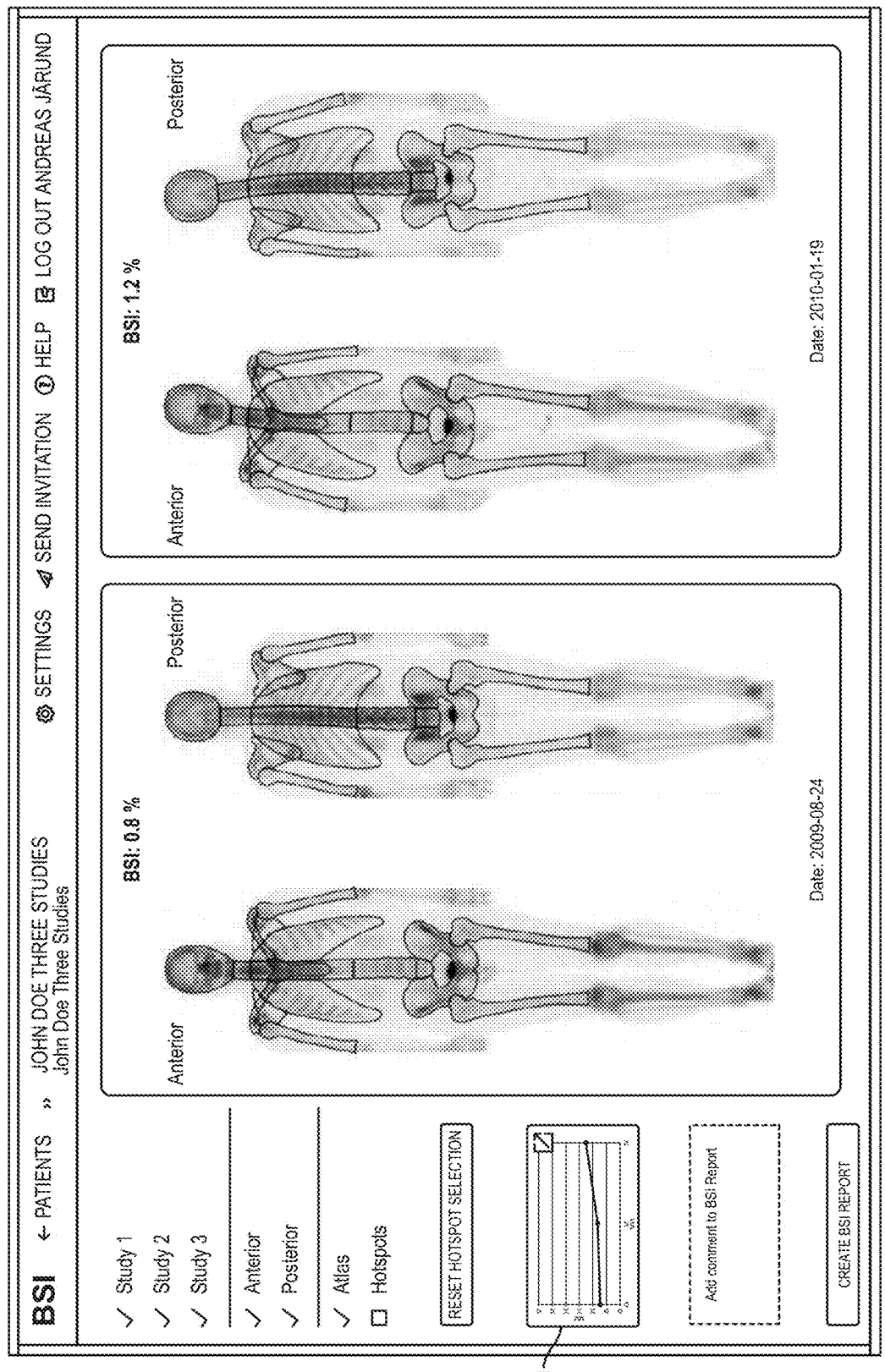
FIG. 4 is a screenshot of a GUI window in the BSI Cloud application showing representative full body gamma camera images showing hotspots automatically identified by the system, with corresponding overall computed BSI values for a particular image set obtained at a given time, according to an illustrative embodiment.

FIG. 4 is a GUI window 400 in the BSI Cloud application showing representative full body gamma camera images showing hotspots automatically identified by the system, with corresponding overall computed BSI values for a particular image set obtained at a given time. A graph 410 at left shows how the BSI value has changed over time (increase) for this particular patient.

Figure 5:
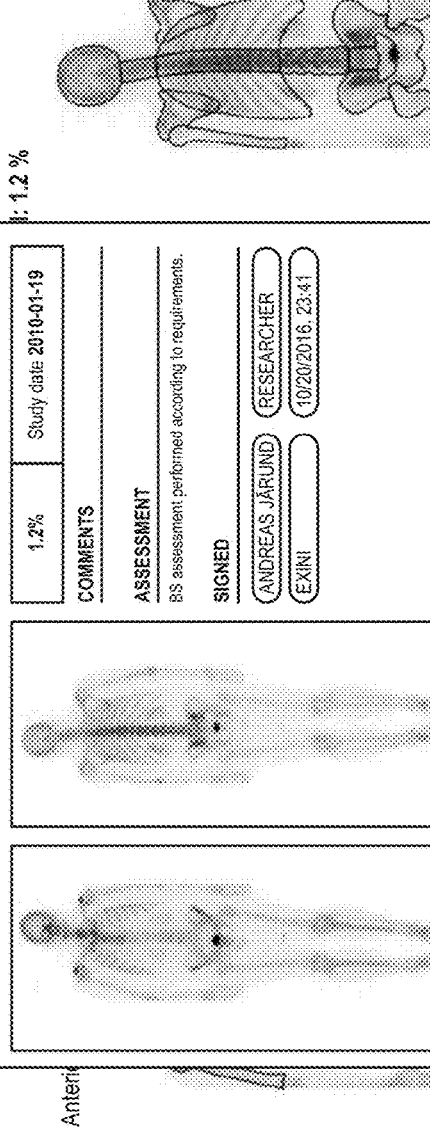
FIG. 5 is a screenshot of a GUI window in the BSI Cloud application showing an automatically or semi-automatically generated radiologist report, which can be signed and dated by a radiologist, according to an illustrative embodiment.

FIG. 5 is a GUI window in the BSI Cloud application showing an automatically or semi-automatically generated radiologist report 510, which can be signed and dated by a radiologist. In certain embodiments, the automatically identified hotspots may be adjusted by the radiologist (or other medical practitioner attending to the patient), with the change(s) reflected in the report. For example, an identified hotspot may be deactivated by the radiologist, or a new hotspot may be activated by the radiologist, such changes possibly affecting the computed BSI value, displayed in the report.

FIG. 6 is a block flow diagram of an illustrative network-based (e.g., cloud based) decision support system, according to an illustrative embodiment of the invention. FIG. 6 shows various functions that may be performed by the cloud based services described herein. These include: (i) receiving and storing sets of medical images in a database; (ii) accessing one or more of the medical images for transmission to the user for display on a user computing device; (iii) automatically analyzing, by the processor, the medical images to compute a risk index (e.g., BSI) and/or to generate a risk map; (iv) generating a radiologist report for a patient according to the patient images and/or risk index/risk map; and applying a machine learning algorithm to update a process for the automatic analysis of function (iii).

Figure 10:
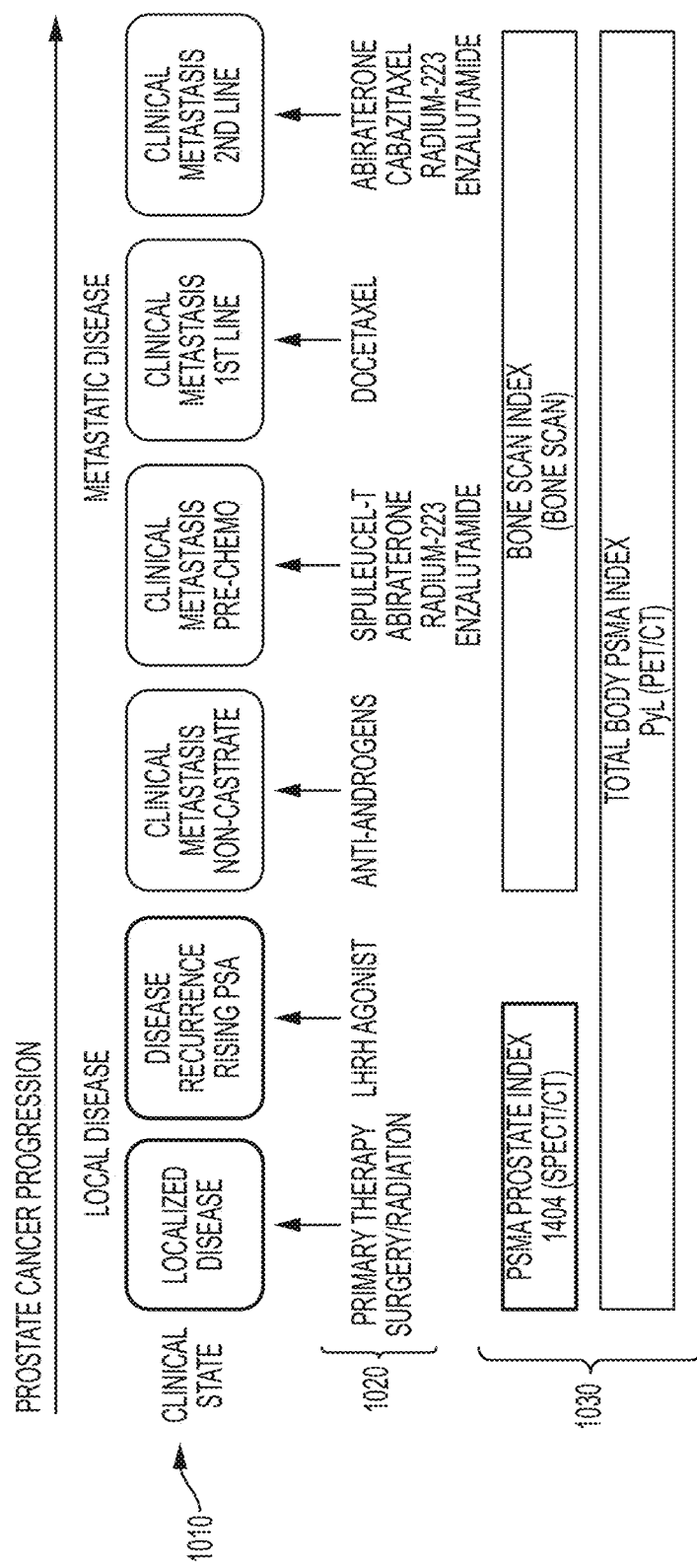
FIG. 10 is a schematic showing stages of prostate cancer progression, along with various therapies and diagnostic imaging modalities appropriate for various disease states, according to an illustrative embodiment.

FIG. 10 is a schematic showing clinical stages 1010 of prostate cancer progression, along with various therapies 1020 and diagnostic imaging modalities 1030 appropriate for various disease states. As shown in the schematic, depending on the clinical state of a patient's prostate cancer, different imaging modalities and/or different radiopharmaceuticals may be appropriate. Similarly, different risk indices computed based on different imaging modalities and/or different radiopharmaceuticals may most appropriate, depending on the state of the patient's prostate cancer.

For example, in certain embodiments, when a patient either has, or is suspected of having prostate cancer in a localized state, composite SPECT-CT imaging may be used. SPECT scans of composite SPECT-CT images used for evaluation of localized prostate cancer can be obtained following administration of a particular radiopharmaceutical, such as $^{99m}$Tc-MIP-1404, that facilitates imaging of localized prostate cancer. Any of the SPECT-CT images themselves, derivatives thereof, and risk indices computed from the SPECT-CT images can be used, accordingly, to assess risk, disease state, progression, treatment efficacy and the like for localized prostate cancer.

In certain embodiments, when a patient has or is suspected of having metastatic prostate cancer, that has metastasized outside of the prostate, other imaging techniques may be used. For example, whole-body scans obtained following administration of $^{99m}$Tc-MDP can be used to assess tumor burden in a patient's skeleton. As discussed above, BSI values computed from whole-body scans can be used to assess risk, disease state, progression, treatment efficacy and the like when a patient's prostate cancer has metastasized to their skeleton. In certain embodiments, certain imaging modalities and/or radiopharmaceuticals can be used for evaluate of prostate cancer in both localized and metastatic states. For example, as illustrated in FIG. 10, PET-CT imaging can be used for evaluating prostate cancer in both localized and metastatic states. As shown in the figure, such PET-CT images may be obtained using an appropriate radiopharmaceutical, such as PyL™, that facilitates imaging of both localized and metastatic prostate cancer.

Figure 11:
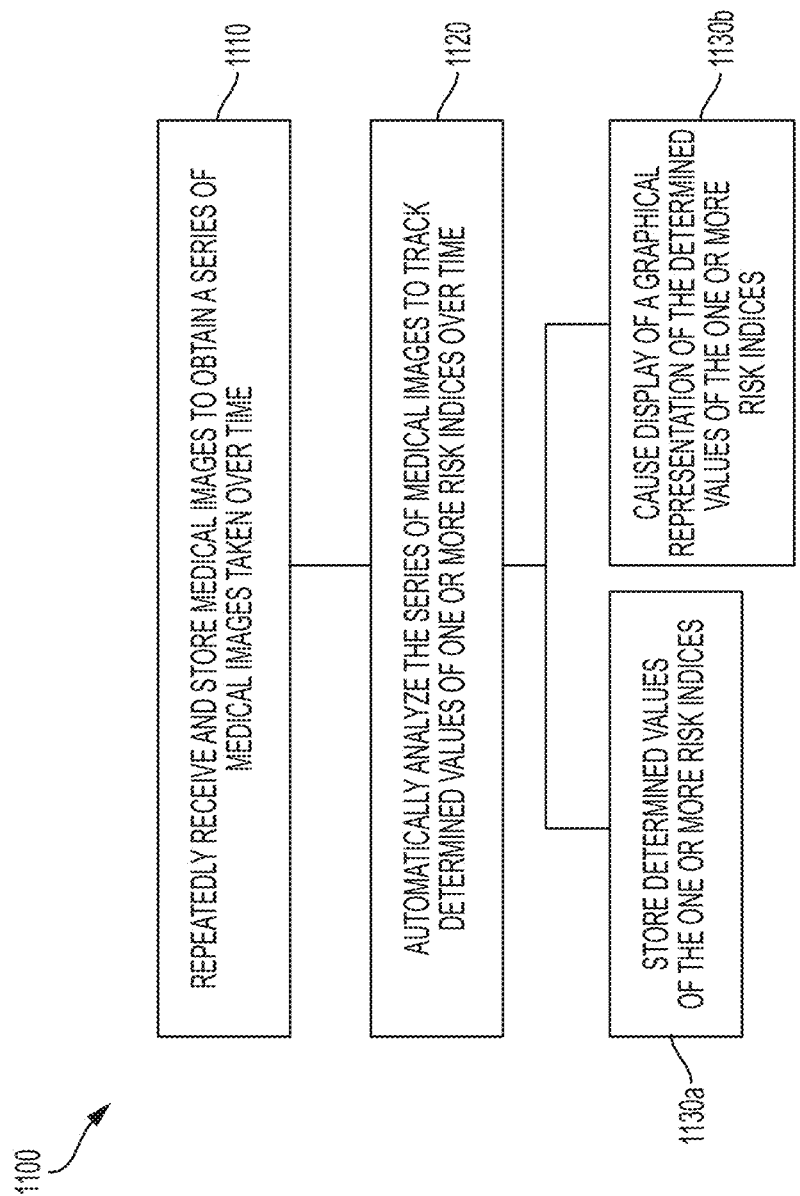
FIG. 11 is a block flow diagram of a process for tracking prostate cancer progression and treatment efficacy over time, according to an illustrative embodiment.

In certain embodiments, the cloud-based platform facilitates evaluating prostate cancer progression and treatment efficacy over time. For example, as shown in the example process 1100 of the block flow diagram of FIG. 11, in certain embodiments medical images of a particular patient are repeatedly received and stored over time 1110, over the course of multiple visits to one or more doctors and/or clinical specialists (e.g., radiologists) by the patient. In this manner, a series of medical images for the patient are obtained. The series of medical images can be automatically analyzed to determine values of one or more risk indices, so as to track changes in the determined values over time 1120. The determined risk index values may be stored 1130a (e.g., for further processing). In certain embodiments, the process causes a graphical representation of the determined risk index values, such as a graph, to be displayed (e.g., on a user computing device; e.g., via a web-based portal) 1130b.

Notably, by virtue of the capability of the cloud-based platform described herein to receive, store, and analyze a variety of different medical image types, such as composite SPECT-CT images, whole-body scans, and composite PET-CT images, the medical images need not be of the same type.

For example, a first subseries of medical images may be obtained using a first imaging modality and a first radiopharmaceutical, such as SPECT-CT imaging with $^{99m}$Tc-MIP-1404, when the patient's prostate cancer is in a localized state. If the patient's prostate cancer progresses to a metastatic state, a second subseries of images may comprise images obtained via a different, second imaging modality and/or a different, second radiopharmaceutical. For example, the second subseries of medical images may be PET-CT images obtained using PyL™ For example, the second subseries of medical images may be whole-body scans obtained using $^{99m}$Tc-MDP.

Risk indices can be computed for the first image subseries and for the second image subseries to provide a unified picture of the patient's prostate cancer progression and treatment over time. This approach can be performed for multiple patients, not only for decision making purposes with regard to each patient's disease progression and particular course of treatment, but also in the context of clinical trials, for example to compare efficacy of a particular treatment with others or a control.

D. Computer System and Network Environment

Figure 7:
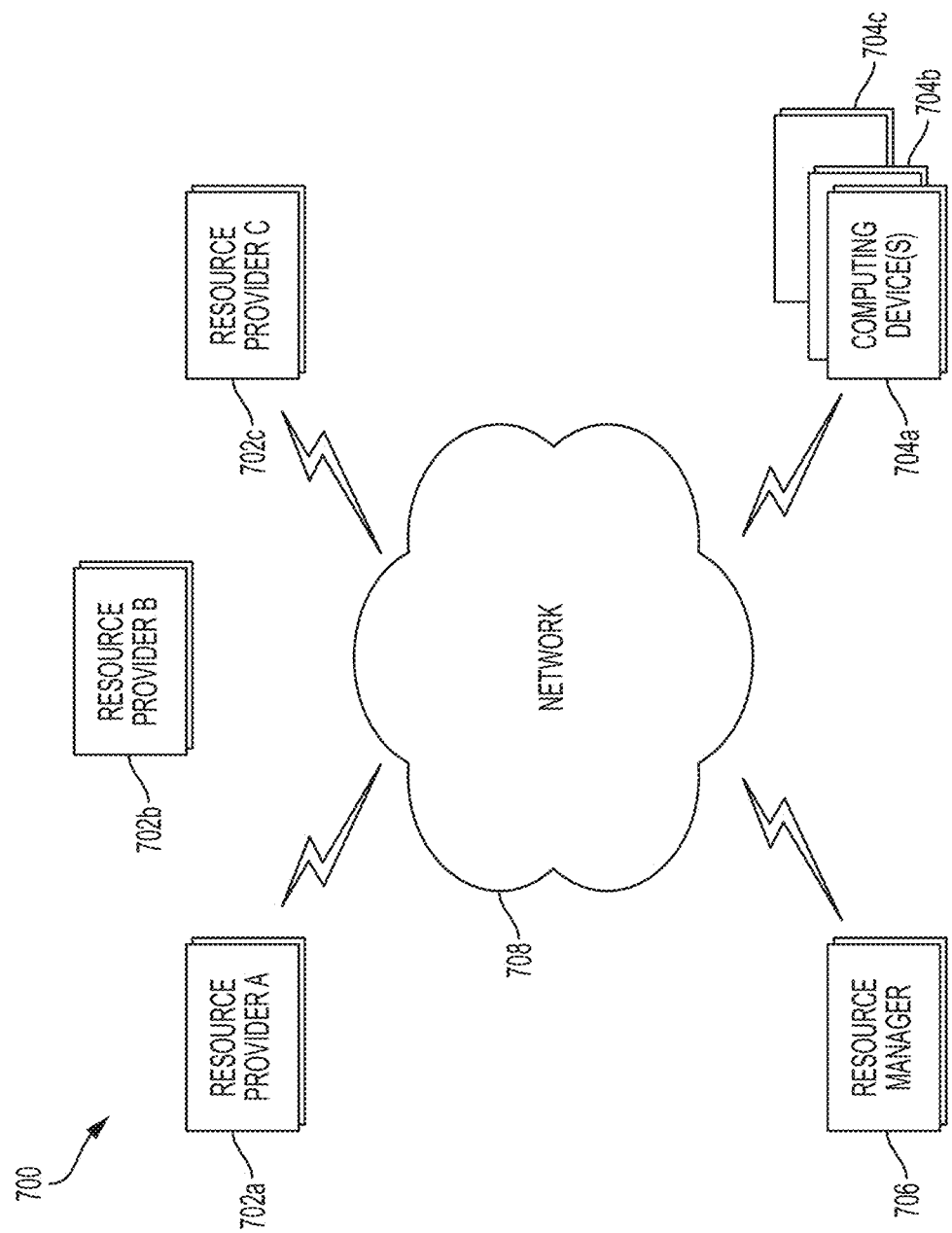
FIG. 7 is a block diagram of an exemplary cloud computing environment, used in certain embodiments.

FIG. 7 shows an illustrative network environment 700 for use in the methods and systems described herein. In brief overview, referring now to FIG. 7, a block diagram of an exemplary cloud computing environment 700 is shown and described. The cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
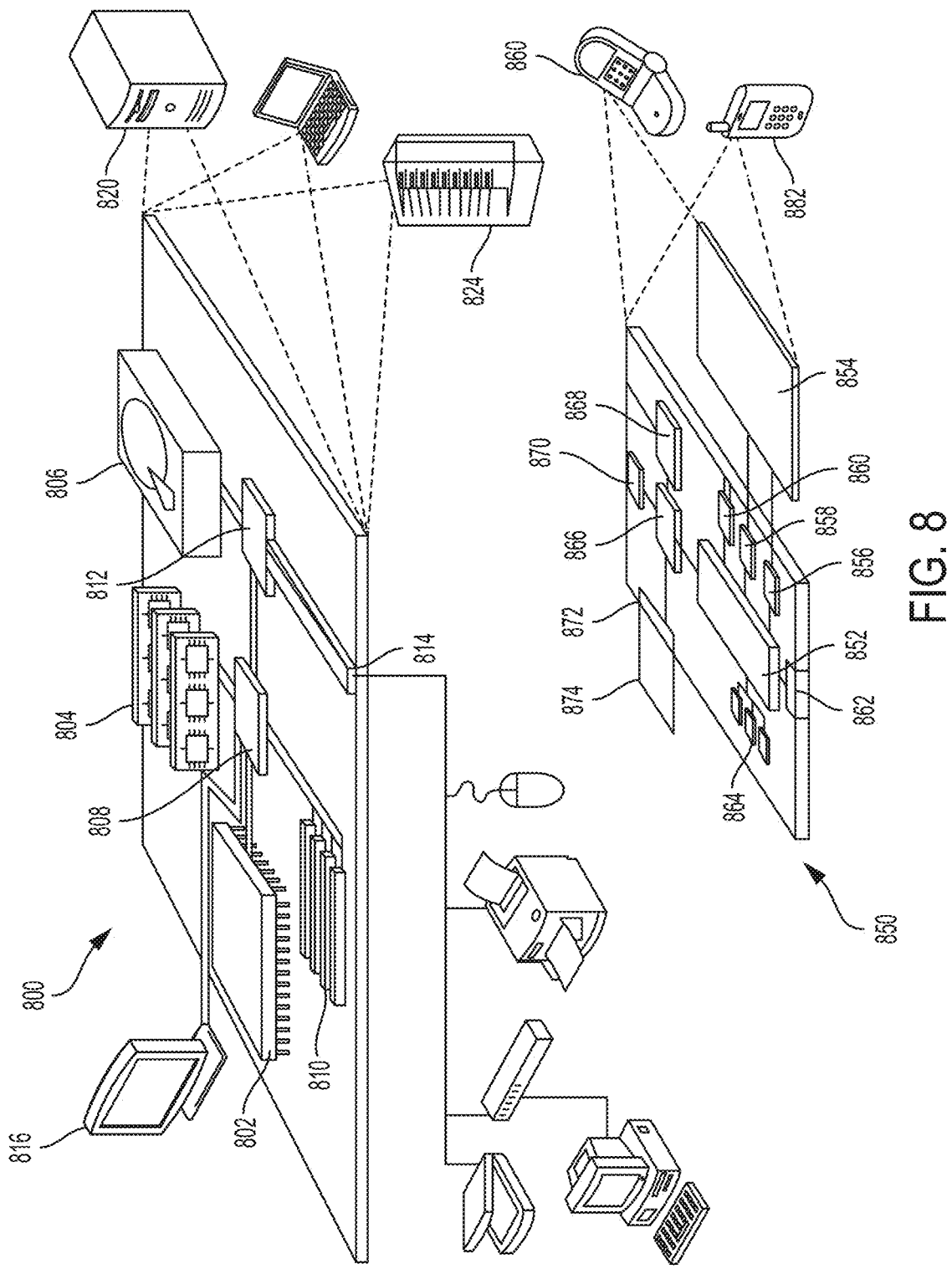
FIG. 8 is a block diagram of an example computing device and an example mobile computing device used in certain embodiments.

FIG. 8 shows an example of a computing device 800 and a mobile computing device 850 that can be used in the methods and systems described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provided as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the modules and/or services (e.g. cloud based services, such as BSI Cloud 110, PyL Cloud 120, 1404 Cloud 130; e.g., any of the microservices described herein) described herein can be separated, combined or incorporated into single or combined modules and/or services. The modules and/or services depicted in the figures are not intended to limit the systems described herein to the software architectures shown therein While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A network-based system for generating a disease risk map for use as a decision-making support for evaluating risk of cancer or risk of recurrence of cancer, the system comprising:
    a processor; and
    a memory having instructions stored thereon, wherein the instructions, when executed by the processor, cause the processor to:
    (i) access one or more medical images associated with a particular patient from a database;
    (ii) perform an analysis of the one or more medical images associated with the particular patient using a machine learning algorithm, to generate the risk map, wherein the risk map comprises a visual representation of tissue overlaid with graphical denotations marking one or more regions of risk of cancer or risk of recurrence of cancer; and
    (iii) cause display of the risk map via a graphical user interface (GUI) for presentation or review of the risk map by a user,
    wherein the analysis of the one or more medical images comprises creation of a 3D image of the one or more regions of risk of cancer or risk of recurrence of cancer overlaid on the one or more medical images, and wherein the 3D image comprises geographic identification of one or more specific tissue region(s) overlaid on the one or more medical images.

2. The system of claim 1, wherein the one or more medical images comprise one or more magnetic resonance images (MRIs).

3. The system of claim 1, wherein the one or more medical images comprise (i) one or more PET/CT image(s) or (ii) one or more SPECT/CT image(s).

4. The system of claim 1, wherein the visual representation of tissue is at least a portion of one of the one or more medical images of the particular patient.

5. The system of claim 1, wherein the cancer is prostate cancer.

6. The system of claim 1, wherein the visual representation of tissue comprises a visual representation of bone.

7. The system of claim 1, wherein the one or more specific tissue region(s) comprise one or more members selected from the group consisting of organs, organ structures, sub-organs, and organ regions.

8. The system of claim 1, wherein the one or more specific tissue region(s) comprise one or more particular bones.

9. The system of claim 1, wherein the instructions cause the processor to generate a radiologist report for the particular patient based at least in part on the analysis of the one or more medical images.

10. The system of claim 9, wherein the radiologist report comprises the one or more medical images and the risk map.

11. The system of claim 9, wherein the radiologist report comprises one or more reference images or reference risk maps.

12. The system of claim 1, wherein the instructions cause the processor to apply a machine learning algorithm to update a process for automatically analyzing the one or more medical images using accumulated image data in the database.

13. A method for generating a disease risk map for use as a decision-making support for evaluating risk of cancer or risk of recurrence of cancer, the method comprising:
    (i) accessing, by a processor, one or more medical images associated with a particular patient from a database;
    (ii) automatically analyzing, by the processor, using a machine learning algorithm, the one or more medical images to generate the risk map, wherein the risk map comprises a visual representation of tissue overlaid with graphical denotations marking one or more regions of risk of cancer or risk of recurrence of cancer; and
    (iii) causing, by the processor, display of the risk map via a graphical user interface (GUI) for presentation or review of the risk map by a user,
    wherein step (ii) comprises creation of a 3D image of the one or more regions of risk of cancer or risk of recurrence of cancer overlaid on the one or more medical images, and wherein the 3D image comprises geographic identification of one or more specific tissue region(s) overlaid on the one or more medical images.

* * * * *